(12) United States Patent
Hiscock et al.

(10) Patent No.: US 10,646,600 B2
(45) Date of Patent: May 12, 2020

(54) HER2 POLYPEPTIDES USEFUL FOR IMAGING AND MONITORING TUMORS AND CANCERS

(71) Applicants: GE HEALTHCARE LIMITED, Chalfont St Giles, Buckinghamshire (GB); IMPERIAL INNOVATIONS LIMITED, London, Greater London (GB)

(72) Inventors: Duncan Robert R. Hiscock, Amersham (GB); Eric Aboagye, London (GB); Peter Iveson, Amersham (GB); Quang-De Nguyen, London (GB); Susan Hoppmann, Amersham (GB); Sebastian Trousil, London (GB); Maciej Kaliszczak, London (GB); Giampaolo Tomasi, London (GB)

(73) Assignees: IMPERIAL INNOVATIONS LIMITED, London (GB); GE HEALTHCARE LIMITED, Buckinghamshire (GB)

( * ) Notice: Subject to any disclaimer, the term of this patent is extended or adjusted under 35 U.S.C. 154(b) by 266 days.

(21) Appl. No.: 14/900,841

(22) PCT Filed: Jun. 24, 2014

(86) PCT No.: PCT/SE2014/050774
§ 371 (c)(1),
(2) Date: Dec. 22, 2015

(87) PCT Pub. No.: WO2014/209205
PCT Pub. Date: Dec. 31, 2014

(65) Prior Publication Data
US 2016/0144062 A1 May 26, 2016

Related U.S. Application Data

(60) Provisional application No. 61/840,021, filed on Jun. 27, 2013.

(51) Int. Cl.
*A61K 51/04* (2006.01)
*A61K 51/10* (2006.01)
*G01N 33/60* (2006.01)

(52) U.S. Cl.
CPC ...... *A61K 51/1051* (2013.01); *A61K 51/1063* (2013.01); *A61K 51/1072* (2013.01); *G01N 33/60* (2013.01); *G01N 2333/4756* (2013.01); *G01N 2800/52* (2013.01)

(58) Field of Classification Search
CPC ............... A61K 51/00; A61K 51/1051; A61K 51/1072; A61K 51/1063; A61K 51/04; G01N 33/60; G01N 2333/4756; G01N 2800/52
USPC .......... 424/1.11, 1.65, 1.69, 1.81, 1.85, 1.89, 424/9.1, 9.2, 9.3, 9.4, 9.411; 514/1, 1.1, 514/19.2, 19.3, 19.4, 19.5, 21.1, 21.2, 514/21.3, 21.4, 21.5, 21.6, 21.7, 21.8, 514/21.9, 21.91; 530/300, 317, 324, 325, 530/326, 327, 328, 329, 330, 331
See application file for complete search history.

(56) References Cited

U.S. PATENT DOCUMENTS

| | | | |
|---|---|---|---|
| 8,017,315 B2 * | 9/2011 | Kufe | A61K 38/1709 435/4 |
| 8,303,960 B2 * | 11/2012 | Capala | A61K 51/1045 424/1.49 |
| 2012/0165650 A1 | 6/2012 | Syud et al. | |
| 2015/0283272 A1 * | 10/2015 | Kundra | A61K 49/1812 424/1.21 |

FOREIGN PATENT DOCUMENTS

| | | |
|---|---|---|
| EP | 3014277 A1 | 5/2016 |
| WO | 2010054699 A1 | 5/2010 |
| WO | 2012087908 A1 | 6/2012 |
| WO | 2012087912 A1 | 6/2012 |
| WO | 2012096760 A1 | 7/2012 |
| WO | 2014/209205 A1 | 12/2014 |

OTHER PUBLICATIONS

Lofblom et al (FEBS Letters, 2010, vol. 584, pp. 2670-2680).*
Office Action received for Chinese Patent Application No. 201480036224.6, dated May 27, 2017, 16 pages.(9 pages of English Translation + 7 pages of Official Copy).
Leyland-Jones et al., "Serum HER2 testing in patients with HER2-positive breast cancer: the death knell tolls", Lancet Oncol, vol. 12, pp. 286-295, 2011.
Malmberg et al., "Comparative biodistribution of imaging agents for in vivo molecular profiling of disseminated prostate cancer in mice bearing prostate cancer xenografts: focus on 111In- and 125I-labeled anti-HER2 humanized monoclonal trastuzumab and ABY-025 affibody", Nucl Med Biol, vol. 38, pp. 1093-102, 2011.
Zagozdzon et al., "Truncated HER2: implications for HER2-targeted therapeutics", Drug Discov Today, vol. 16, pp. 810-816, 2011.

(Continued)

*Primary Examiner* — D. L. Jones
(74) *Attorney, Agent, or Firm* — Arent Fox, LLP

(57) ABSTRACT

A method of use of an isolated polypeptide conjugated with a radionuclide, wherein the isolated polypeptide binds specifically to HER2, or a variant thereof is described. The method is for monitoring the response to HSP90 inhibition and comprises the use of the isolated polypeptide conjugated with 18F. The application also describes the use of an isolated polypeptide conjugated with 18F, wherein the isolated polypeptide binds specifically to HER2 or variants thereof, as an imaging agent to monitor uptake thereof to measure HSP90 inhibition.

5 Claims, 15 Drawing Sheets

Specification includes a Sequence Listing.

(56) References Cited

OTHER PUBLICATIONS

Kramer-Marek et al., "PET of HER2-positive pulmonary metastases with 18F-ZHER2:342 affibody in a murine model of breast cancer: comparison with 18F-FDG", J Nucl Med , vol. 53, pp. 939-946, 2012.
Kramer-Marek et al., "Potential of PET to predict the response to trastuzumab treatment in an ErbB2-positive human xenograft tumor model", J Nucl Med, vol. 53, pp. 629-637, 2012.
Malmberg et al., "Comparative evaluation of synthetic anti-HER2 Affibody molecules site-specifically labelled with 111In using N-terminal DOTA, NOTA and NODAGA chelators in mice bearing prostate cancer xenografts", Eur J Nucl Med Mol Imaging , vol. 39, pp. 481-492, 2012.
Orlova et al., "Site-Specific Radiometal Labeling and Improved Biodistribution Using ABY-027, A Novel HER2—Targeting Affibody Molecule-Albumin-Binding Domain Fusion Protein", J Nucl Med, 2013.
Shafi et al., "Clinicopathological significance of HER2/neu genetic heterogeneity in HER2/neu non-amplified invasive breast carcinomas and its concurrent axillary metastasis", J Clin Pathol, 2013.
Xavier et al., "Synthesis, Preclinical Validation, Dosimetry, and Toxicity of 68Ga-NOTA-Anti-HER2 Nanobodies for PET Imaging of HER2 Receptor Expression in Cancer", J Nucl Med, 2013.
International Search Report and Written Opinion issued in connection with corresponding Application No. PCT/SE2014/050774 dated Oct. 15, 2014.
Trousil S. et al., "Positron Emission Tomography imaging with 18F-Labeled ZHERE2:2891 Affibody for detection of Her2 expression and pharmacodynamic response to Her2-Modulating Therapies", pp. 1632-1643, 2014.
Scaltriti et al., "Expression of p95HER2, a truncated form of the HER2 receptor, and response to anti-HER2 therapies in breast cancer", J Natl Cancer Inst , vol. 99, pp. 628-638, 2007.
Tolmachev et al., "Affibody molecules: potential for in vivo imaging of molecular targets for cancer therapy", Expert Opin Biol Ther , vol. 7, pp. 555-568, 2007.
Tuefferd et al., "HER2 Status in Ovarian Carcinomas: A Multicenter GINECO Study of 320 Patients", PLoS One , vol. 2, pp. e1138, 2007.
Valabrega et al., "Trastuzumab: mechanism of action, resistance and future perspectives in HER2-overexpressing breast cancer", Ann Oncol, 2007.
Eccles et al., "NVP-AUY922: A Novel Heat Shock Protein 90 Inhibitor Active against Xenograft Tumor Growth, Angiogenesis, and Metastasis", Cancer Res , vol. 68, pp. 2850-2860, 2008.
Gravalos et al., "HER2 in gastric cancer: a new prognostic factor and a novel therapeutic target", Ann Oncol , vol. 19, pp. 1523-1529, 2008.
Nygren "Alternative binding proteins: Affibody binding proteins developed from a small three-helix bundle scaffold", FEBS J , vol. 275, pp. 2668-2676, 2008.
Gill. H. S. et al., "A Modular platform for the rapid site-specific radio radiolabeling of proteins with 18F exemplified by quantitative position emission tomography of human epidermal growth factor receptor2", J.Med. Chem., vol. 52, pp. 5816-5825, 2009.
Kramer-Marek et al., "Changes in HER2 expression in breast cancer xenografts after theraphy can be quantified using PET and (18)F-labelled affibody molecules", J Nucl Med, vol. 50, pp. 1131-1139, 2009.
Tomasi et al., "Voxel-based estimation of kinetic model parameters of the L[1-(11)C]leucine PET method for determination of regional rates of cerebral protein synthesis: validation and comparison with region-of-interest-based methods", J Cereb Blood Flow Metab , vol. 29, pp. 1317-1331, 2009.
Ahlgren et al., "Targeting of HER2-expressing tumors using 111In-ABY-025, a second-generation affibody molecule with a fundamentally reengineered scaffold", J Nucl Med , vol. 51, pp. 1131-1138, 2010.
Baum et al., "Molecular Imaging of HER2-Expressing Malignant Tumors in Breast Cancer Patients Using Synthetic 111In- or 68Ga-Labeled Affibody Molecules", J Nucl Med , vol. 51, pp. 892-897, 2010.
Feldwisch et al., "Design of an optimized scaffold for affibody molecules", J Mol Biol , vol. 398, pp. 232-247, 2010.
Lofblom et al., "Affibody molecules: Engineered proteins for therapeutic, diagnostic and biotechnological applications", FEBS Leff , vol. 584, pp. 2670-2680, 2010.
Oude et al., "89Zr-trastuzumab PET visualises HER2 downregulation by the HSP90 inhibitor NVP-AUY922 in a human tumour xenograft", Eur J Cancer, vol. 46, pp. 678-684, 2010.
Sakamoto J.H. et. al., "Enabling individualized therapy through nanotechnology", pharmacological research, vol. 62. pp. 57-89, 2010.
Fabi et al., "HER2 Protein and Gene Variation between Primary and Metastatic Breast Cancer: Significance and Impact on Patient Care", Clin Cancer Res, vol. 17, pp. 2055-2064, 2011.
Hoppmann et al., "Radiolabeled Affibody—Albumin Bioconjugates for HER2-Positive Cancer Targeting", Bioconj Chem , vol. 22, pp. 413-421, 2011.
Iveson P.B. et al., "Fluorine-18 Labelling and Biological evaluation of the Her2-binding affibody molecule ZHERE2:2891", Eur J Nucl Med Mol Imaging, vol. 38, Suppl. 2, S184, 2011.
McKenzie et al.,"Serum levels of HER-2 neu (C-erbB-2) correlate with over expression of p185neu in human ovarian cancer", Cancer, vol. 71, pp. 3942-3946, 1993.
Pauletti et al., "Detection and quantitation of HER-2/neu gene amplification in human breast cancer archival material using fluorescence in situ hybridization", Oncogene , vol. 13, pp. 63-72, 1996.
Behr et al., "Reducing the renal uptake of radiolabeled antibody fragments and peptides for diagnosis and therapy: present status, future prospects and limitations", Eur J Nucl Med , vol. 25, pp. 201-212, 1998.
Ross et al., "The HER-2/neu oncogene in breast cancer: Prognostic factor, predictive factor, and target for therapy", Stem Cells, vol. 16, pp. 413-428, 1998.
Harari et al., "The ErbB signaling network: receptor heterodimerization in development and cancer", EMBO J, vol. 19, pp. 3159-3167, 2000.
Olayioye et al., "The ErbB signaling network: receptor heterodimerization in development and cancer", EMBO J, vol. 19, pp. 3159-3167, 2000.
Carlsson et al., "HER2 expression in breast cancer primary tumours and corresponding metastases. Original data and literature review", Br J Cancer, vol. 90, pp. 2344-2348, 2004.
Smith-Jones et al., "Imaging the pharmacodynamics of HER2 degradation in response to Hsp90 inhibitors", Nat Biotech, vol. 22, pp. 701-706, 2004.
Calderwood et al., "Heat shock proteins in cancer: chaperones of tumorigenesis", Trends Biochem Sci , vol. 31, pp. 164-172, 2006.
Orlova et al., "Tumor imaging using a picomolar affinity HER2 binding affibody molecule", Cancer Res , vol. 66, pp. 4339-4348, 2006.
Shukla et al., "HER2 Specific Tumor Targeting with Dendrimer Conjugated Anti-HER2 mAb", Bioconj Chem , vol. 17, pp. 1109-1115, 2006.
Tolmachev et al., "In-111-benzyl-DTPA-Z(HER2 : 342), an affibody-based conjugate for in vivo imaging of HER2 expression in malignant tumors", J Nucl Med , vol. 47, pp. 846-853, 2006.
Workman et al., "Minimally invasive pharmacokinetic and pharmacodynamic technologies in hypothesis-testing clinical trials of innovative therapies", J Natl Cancer Inst , vol. 98, pp. 580-598, 2006.
Hudis et al., "Mechanism of Action and Use in Clinical Practice", New Engl J Med , vol. 357, pp. 39-51, 2007.
Orlova et al., "Synthetic Affibody Molecules: A Novel Class of Affinity Ligands for Molecular Imaging of HER2—Expressing Malignant Tumors", Cancer Res , vol. 67, pp. 2178-2186, 2007.
Extended European Search Report received for European Patent Application No. 14816932.9, dated Mar. 20, 2017, 10 pages.

(56) References Cited

OTHER PUBLICATIONS

International Preliminary Report on Patentability received for PCT Patent Application No. PCT/SE2014/050774, dated Dec. 29, 2015, 12 pages.

* cited by examiner

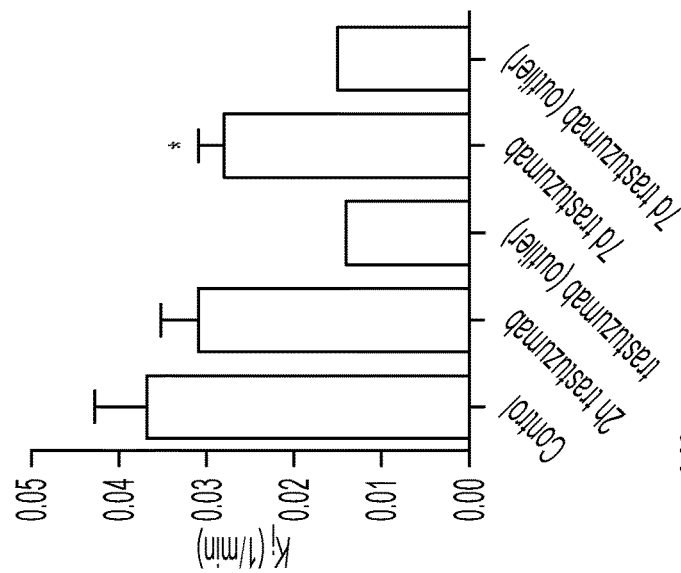
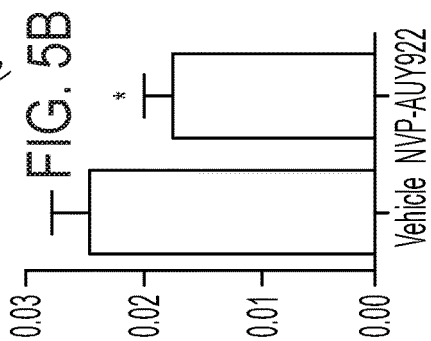
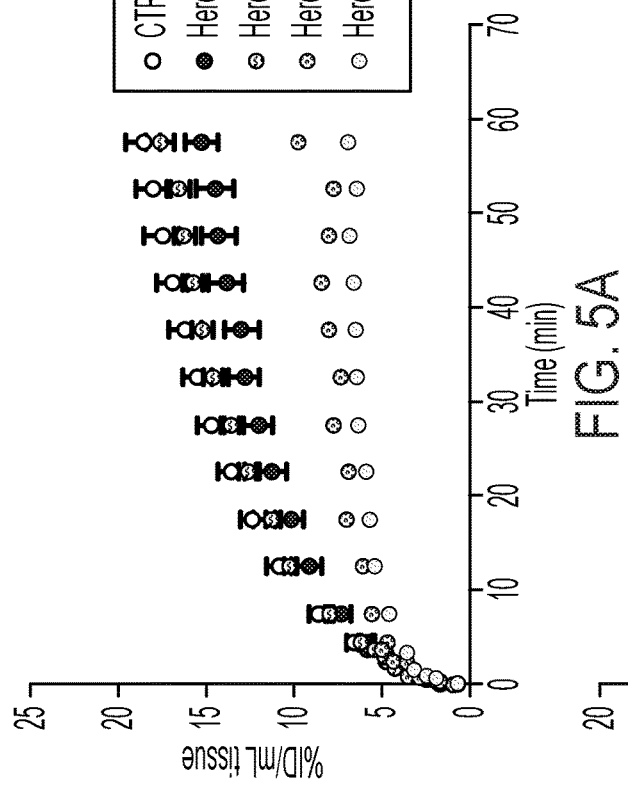
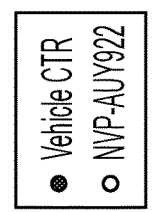
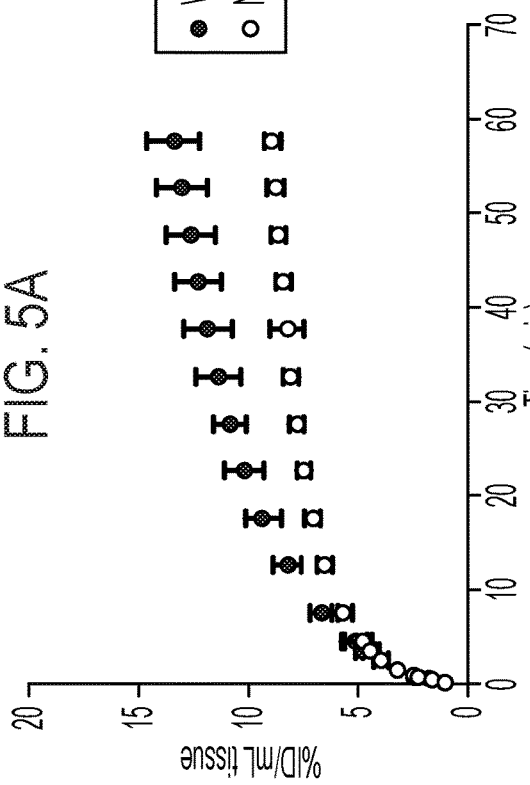

SEQUENCE LISTING

<160> NUMBER OF SEQ ID NOS: 1

<210> SEQ ID NO 1
<211> LENGTH: 60
<212> TYPE: PRT
<213> ORGANISM: Artificial Sequence
<220> FEATURE:
<223> OTHER INFORMATION: Synthetic polypeptide

<400> SEQUENCE: 1

```
Ala Glu Ala Lys Tyr Ala Lys Glu Met Arg Asn Ala Tyr Trp Glu Ile
1               5                   10                  15

Ala Leu Leu Pro Asn Leu Thr Asn Gln Gln Lys Arg Ala Phe Ile Arg
            20                  25                  30

Lys Leu Tyr Asp Asp Pro Ser Gln Ser Ser Glu Leu Leu Ser Glu Ala
        35                  40                  45

Lys Lys Leu Asn Asp Ser Gln Ala Pro Lys Val Asp
    50                  55                  60
```

HER2 POLYPEPTIDES USEFUL FOR IMAGING AND MONITORING TUMORS AND CANCERS

STATEMENT REGARDING SEQUENCE LISTING

The Sequence Listing associated with this application is part of the description and is provided in text the form of an Annex C/ST.25 text file in lieu of a paper copy, and is hereby incorporated by reference into the specification. The name of the text file containing the Sequence Listing is "PZ1335 PCT Sequence Listing_ST25.txt." The text file is 1.09 kb, and is being submitted electronically via EFS-Web.

BACKGROUND

Embodiments of the present invention relate to a method of use of an isolated polypeptide conjugated with a radionucleide; wherein the isolated polypeptide binds specifically to HER2, or a variant thereof.

Human Epidermal Growth Factor Receptor 2 (HER2, also referred to as HER2/neu or ErbB-2) is a 185 kDa transmembrane receptor belonging to the epidermal growth factor receptor family (1). HER2 gene amplification and protein over-expression play pivotal roles in the pathogenesis and progression of many types of cancer. HER2 is overexpressed in 25-30% of breast, 15-35% of gastric and 7-38% of ovarian cancers and is correlated with poor survival (2-5). The protein has consequently emerged in recent years as an important predictive biomarker and target of cancer therapy (6). Homo- or heterodimerization with other members of its family prompts activation of the intracellular tyrosine kinase domain and triggers cell survival and proliferation mediated through MAPK and Akt signaling pathways (7, 8).

Available HER2-targeted therapies in the clinic include antibodies, such as trastuzumab (Herceptin, Genentech) and pertuzumab (Perjeta, Genentech), which prevents receptor dimerization, antibody-drug conjugates, such as T-DM1 (Kadcyla, Genentech) or small molecule inhibitors targeting the tyrosine-kinase domain (e.g. lapatinib, Tyverb, GlaxoSmithKline; a dual HER2 and EGFR inhibitor). Proteolytic shedding of the extracellular domain or alternative splicing in limited cases can generate a truncated, signaling remnant p95HER2 domain, which presents one of the most prominent mechanism of resistance to anti-HER2 therapies (9). Although trastuzumab forms the mainstay of anti-HER2 targeted therapies, it does not reverse HER2 protein expression. Inhibitors of the molecular chaperone HSP90, which elicit HER2 proteasomal degradation, are therefore currently under investigation in this context. One such inhibitor, NVP-AUY922 (Novartis) is in phase II clinical trials.

Accurate testing of HER2 status is crucial for patient stratification to identify individuals that may benefit most from such targeted therapies, notably trastuzumab or pertuzumab. However, this can be intricate as HER2 expression may vary through progression from primary to secondary disease with locoregional and distant recurrences often not being amenable to biopsy (10). Furthermore, recent studies have highlighted spatial heterogeneity as a potential source of incorrect assessment (11). The vast majority of FDA-approved diagnostics are based on immunohistochemistry (IHC) and fluorescence in situ hybridization (FISH). IHC determines the HER2 protein expression in formalin-fixed paraffin embedded (FFPE) tumor biopsies, while FISH detects HER2 gene amplifications, which are considered a legitimate surrogate as HER2 overexpression is generally caused by copy number variations (12). The utility of serum-based alternatives by detecting soluble extracellular domains is also under investigation (13).

Tumor marker-targeted molecular imaging using radiolabeled Affibody molecules, which are non-immunoglobulin-derived affinity proteins, might provide an accurate and non-invasive alternative to HER2 molecular diagnostics. Affibody molecules are engineered as three-helix bundle Z proteins derived from the staphylococcal protein A (14). They are characterized by nano- to picomolar binding affinities, small size of ~6.5 kDa compared to antibodies or antibody fragments (~20-150 kDa), and short plasma residence time, thus permitting rapid and homogenous tissue distribution. Consequently, high contrast images can be obtained within the first h or two of administration (15, 16). Furthermore, these molecules are highly suitable for radiolabeling with short-lived radioisotopes by comparison with full IgG antibodies.

Accurate assessment of a cancer patient's HER2 status remains a clinical challenge with up to 20% of patients being potentially withdrawn from therapy or exposed to unnecessary toxicity. Non-invasive imaging is widely seen as a viable alternative to current methods, in particular within the setting of locoregional and distant recurrences not amenable to biopsy, but clinical success by positron emission tomography has so far been hampered by prolonged tracer retention in liver and kidneys obstructing detection on proximate metastases.

SUMMARY OF THE INVENTION

It has now been found that the HER2-targeting Affibody [$^{18}$F]GE-226 provides a viable strategy to determine differential HER2 expression irrespective of lineage or pre-treatment with trastuzumab within 1 h after injection. Insights into the kinetic characteristics of the Affibody interaction with HER2 using full length versus p95HER2 transfected cells and siRNA HER2 as controls, or HSP90 inhibitor treatment to degrade HER2 are provided herein.

Embodiments of the present invention, as described below, provide a method of use of a HER2 binder to monitor response to HSP90 inhibition.

Embodiments of the present invention provide a method to monitor response to HSP90 inhibition comprising the steps of: administering an isolated polypeptide conjugated with 18F wherein the isolated polypeptide binds specifically to HER2 or variants thereof to a subject; and imaging the subject; and monitoring uptake of the imaging agent composition to measure HSP90 inhibition. Embodiments of the present invention also relate to use of the polypeptide as an imaging agent.

BRIEF DESCRIPTION OF THE DRAWINGS

FIGS. 5A-5D shows [18F]GE-226[SEQ ID NO 1] binding does not interfere with trastuzumab treatment and can predict response to HSP90 inhibition: (5A) Mice bearing SKOV-3 xenografts were treated with 50 mg/kg trastuzumab i.p. 2 h prior to scan. Animals were recovered, treated twice more with 25 mg/kg trastuzumab and re-imaged 7 days after initial scan (n=6±SEM). One mouse, which was an outlier with low tracer uptake both on early and late scan and is displayed separately, (5B) Pharmacokinetic analysis of A (P=0.025), (5C) Comparison of NVP-AUY922 treatment (n=5±SEM) to vehicle treated controls (n=4±SEM) in the SKOV-3 xenograft model and (5D) kinetic analysis of inhibition constants (P=0.011).

DETAILED DESCRIPTION

Figure 1A:
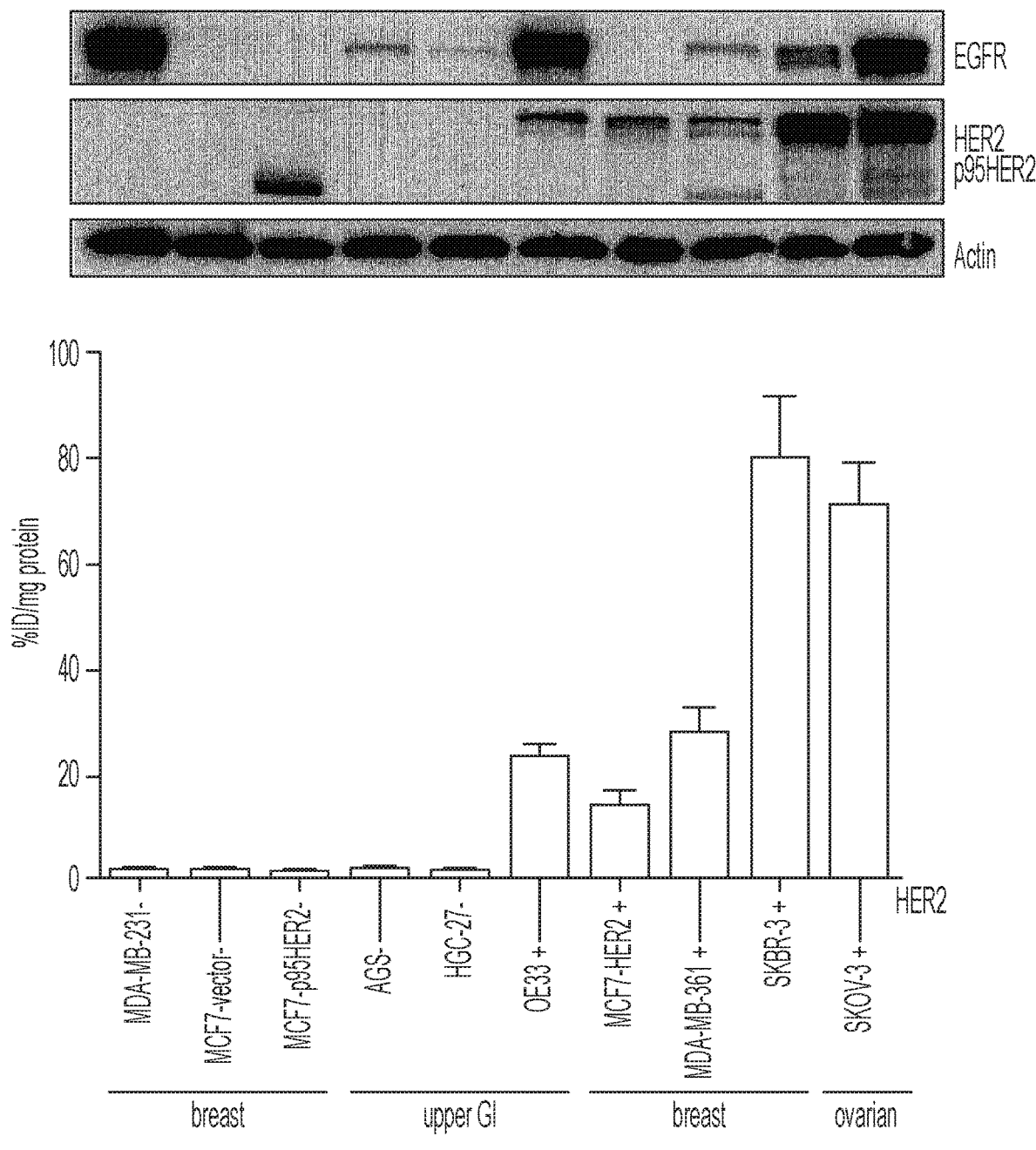
FIGS. 1A-1B show [$^{18}$F]GE-226[SEQ ID NO 1] binds with high selectively and sensitivity to HER2: (1A) Cell lines of diverse lineages and differential HER2 status were exposed to [$^{18}$F]GE-226 [SEQ ID NO 1] for 60 minutes and retained radioactivity measured as percent applied radioactivity normalized to total protein (mean of n=1 with 5-6 replicates±SD). Full length and truncated p95HER2 protein expression as determined by western blot is shown for the same cell lines in the panel above, (1B) SKOV-3 cells were incubated with [$^{18}$F]GE-226[SEQ ID NO 1] in the presence or absence of 0.5 mg/mL blocking dose of [$^{19}$F]GE-226 [SEQ ID NO 1] for 60 minutes and cell-bound activity measured (P<0.0001; mean of n=3 in triplicate on three different days±SD), (C) HER2 expression was transiently abrogated by siRNA and tracer retention after 60 minutes compared to non-targeting scramble control (P<0.0001; mean of n=3 in triplicate on three different days±SD); knock-down confirmed by western blot.

The isolated polypeptide can be any polypeptide that binds specifically to HER2 or variants thereof conjugated or labeled with a radioisotope suitable for diagnostic imaging. While not being limited thereto, examples of suitable isolated polypeptides and radiolabeled derivatives thereof and methods of making the same can be found in WO2012/096760, WO2012/087908 and WO2012/087912, each of which is incorporated herein in its entirety by reference. More particularly, the isolated polypeptide comprises SEQ. ID No. 1, or a conservative variant thereof, as described in WO2012/096760, WO2012/087908 and WO2012/087912, each of which is incorporated herein in its entirety by reference. More particularly, the isolated polypeptide is HER2-binding 18F-radiolabelled Affibody® molecule ZHER2:2891 [SEQ ID NO 1] referred herein as [18F]GE-226[SEQ ID NO 1] and described in the Sequence listing.

Examples

Experimental design: Intrinsic cellular [18F]GE-226 [SEQ ID NO 1] uptake and tumor-specific tracer binding were assessed in cells and xenografts with and without drug treatment. Specificity was further determined by comparing tumor localization of a fluorescently labeled analogue with DAKO HercepTest™.

Results: [$^{18}$F]GE-226[SEQ ID NO 1] uptake was 11 to 67-fold higher in ten HER2 positive versus negative cell lines in vitro independent of lineage. Uptake in HER2 positive xenografts was rapid with net irreversible binding kinetics making possible the distinction of HER2 negative (MCF7 and MCF7-p95HER2: $NUV_{60}$ (% ID/mL) 6.1±0.7; $K_i$ (mL/cm$^3$/min) 0.0069±0.0014) from HER2 positive tumors ($NUV_{60}$ and $K_i$: MCF7-HER2, 10.9±1.5 and 0.015±0.0035; MDA-MB-361, 18.2±3.4 and 0.025±0.0052; SKOV-3, 18.7±2.4 and 0.036±0.0065) within 1 h. Tumor uptake correlated with HER2 expression determined by ELISA ($r^2$=0.78), and co-localized with HER2 expression at the cellular level. Tracer uptake was not influenced by short-term or continuous treatment with trastuzumab in keeping with differential epitope binding, but reflected HER2 degradation by short-term NVP-AUY922 treatment in SKOV-3 xenografts ($NUV_{60}$: 13.5±2.1 versus 9.0±0.9% ID/mL for vehicle or drug, respectively).

Results

Conclusions: [$^{18}$F]GE-226[SEQ ID NO 1] binds with high specificity to HER2 independent of cell lineage. The tracer has utility for HER2 detection, irrespective of prior trastuzumab treatment, and to monitor response to HSP90 inhibition.

Materials and Methods

Intrinsic affinity to HER2 ($K_D$=76 pM) resulted in 11 to 67-fold higher [$^{18}$F]GE-226 uptake in ten HER2 positive versus negative cell lines in vitro independent of lineage. Uptake correlated with HER2 protein expression but was independent of presence of other targets like EGFR. Blocking with [$^{19}$F]GE-226[SEQ ID NO 1] and HER2 siRNA treatment reduced uptake by 96.8±2.6% and 81.7±9.2%, respectively. Uptake in HER2 positive xenografts was rapid with steady state net irreversible binding kinetics making possible the distinction of HER2 negative (MCF7 and MCF7-p95HER2: $NUV_{60}$ (% ID/mL) 6.1±0.7; $K_i$ (mL/cm$^3$/min) 0.0069±0.0014) from HER2 positive tumors ($NUV_{60}$ and $K_i$: MCF7-HER2, 10.9±1.5 and 0.015±0.0035; MDA-MB-361, 18.2±3.4 and 0.025±0.0052; SKOV-3, 18.7±2.4 and 0.036±0.0065) within 1 h. Tumor uptake correlated with HER2 expression determined by ELISA ($r^2 \geq 0.74$, when the variable was $NUV_{60}$ or $K_i$). Specificity was further determined by comparing tumor localization of a fluorescently labeled tracer analogue with DAKO HercepTest™. Affibody tumoral signal co-localized with HER2 expression at the cellular level independent of spatial heterogeneity. Tracer binding was not influenced by short-term or continuous exposure to trastuzumab in SKOV-3 xenografts (50 mg/kg i.p. bolus followed by two doses of 25 mg/kg i.p over a total of 7 days) in keeping with differential epitope binding. Inhibition of the chaperone HSP90—of which HER2 is a client protein—by NVP-AUY922 caused dose-dependent HER2 degradation and consequently reduced tracer uptake in SKOV-3 cells in vitro, and in vivo after three daily doses of 50 mg/kg NVP-AUY922 in SKOV-3 xenografts ($AUC_{0\_60}$: 618.4±90.1 versus 446.7±42.8% ID/mL*min for vehicle and drug, respectively; P=0.043).

Chemistry and Radiochemistry [$^{18}$F]GE-226[SEQ ID NO 1] was labeled using a fluorobenzaldehyde (FBA) strategy optimized for automated manufacture on FASTlab. Briefly, the radiochemistry uses a maleimide-aminooxyacetyl Affibody molecule precursor, which is conjugated to a [$^{18}$F] fluorobenzaldehyde synthon followed by solid phase extraction (SPE) product purification. Typical non-decay corrected end of synthesis yields were 25% and a radiochemical purity of 95%.

Surface Plasmon Resonance

To characterize the affinity of [$^{19}$F]GE-226[SEQ ID NO 1] to HER2 protein, Surface Plasmon Resonance studies were conducted. Human, rhesus and rat HER2-ECD-Fc (SINO Biological, Beijing, China, Cat. Nr: 10004-H02H, 90020-K02H, and 80079-R02H), as well as human HER2-ECD-Fc-6×His (R&D Systems, Minneapolis, Minn., Cat. Nr: 1129-ER) and p95HER2 ECD-Fc-6×His (Syngene, Cambridge, United Kingdom) were diluted with 50 mM sodium acetate pH 4.5 (Biacore (GE Healthcare, Buckinghamshire, UK) coupling buffer) to a final concentration of 10 µg/mL. Antigen coupling to Biacore sensor chip CM5 (Cat. Nr: BR-1005-30) was done according to amine coupling protocol from the instrument manual (Syngene). HBS-EP buffer (10 mM HEPES pH 7.4, 150 mM NaCl, 3 mM EDTA and 0.005% surfactant P20; GE Healthcare, Little Chalfont, United Kingdom, Cat. Nr: BR-1006-69) was used as running buffer and as solvent for the substances. The affinity studies were performed using a Biacore T100 (GE Healthcare). [$^{19}$F]GE-226 was diluted in HBS-EP buffer to 50 nM, 25 nM, 12.5 nM, 6.25 nM, 3.125 nM, 1.56 nM, 0.78 nM, 0.39 nM, 0.195 nM, 0.097 nM, 0.049 nM and 0 nM. The flow cells of the first chip comprised of blank, human HER2-ECD-Fc-6×His, p95HER2-ECD-Fc-6×His batch I and p95HER2-ECD-Fc-6×His batch II. The flow cells on the second chip contained blank, human HER2-ECD-Fc, rhesus HER2-ECD-Fc and rat HER2 ECD-Fc. The immobilization of the proteins was validated with protein-A (Sigma-Aldrich, St. Louis, Mo., Cat. Nr: P6031) and anti-human IgG antibody (Perkin Elmer, Waltham, Mass., Cat. Nr: NEF803001EA). [$^{19}$F]GE-226[SEQ ID NO 1] was pumped in duplicate over cells in randomized order for 60 sec at 50 µL/min flow rate followed by 120 sec of HBS-EP to monitor dissociation. This was followed by regeneration of the chip with 50 mM sodium hydroxide for 30 sec at 30 µL/min flow rate followed by 60 sec run of HBS-EP to stabilize the surface. Kinetic calculations were performed using Langmuir 1:1 binding model and simultaneous calculation of association and dissociation phase.

Cells and Treatments

MCF7-vector (piRES), MCF7-p95HER2 and MCF7-HER2 cells were a kind gift of Jose Baselga's laboratory (17). MCF7 clones, MDA-MB-231 (ATCC, Manassas, Va.), MDA-MB-361 (Sigma-Aldrich), SKBR-3 (ATCC) and SKOV-3 (Sigma-Aldrich) cells were maintained in DMEM. AGS (Sigma-Aldrich), HGC-27 (Sigma-Aldrich), NCI-N87 (ATCC) and OE-33 (ATCC) cells were maintained in RPMI (Sigma-Aldrich). A431 cells (Sigma-Aldrich) were maintained in MEM Eagle medium (Sigma-Aldrich). Growth media were supplemented with 10% FCS (Lonza, Basel, Switzerland), glutamine and antibiotics (both Invitrogen, Paisley, United Kingdom). A431 cells were additionally supplemented with 1% non-essential amino acids. All cells were cultured at 37° C. in a humidified atmosphere containing 5% $CO_2$.

For siRNA-mediated HER2 knockdown, SKOV-3 cells were transfected with 25 nM scramble control (SCR; Dharmacon, Lafayette, Colo., ON-TARGETplus Non-targeting Pool, Cat. Nr: D-001810-10-05) or HER2-targeting siRNA (Invitrogen ERBB2 Silencer® Select Validated siRNA; Cat. Nr: 4457298) by reverse wet transfection with Lipofectamine RNAiMAX (Invitrogen) according to manufacturer's instructions. $3 \times 10^5$ cells were seeded in 12-well plates 48 h prior to uptake experiment. Target knockdown was verified by western blotting on cells that were transfected in parallel.

For all uptake studies in response to drug treatment, $2.5 \times 10^5$ SKOV-3 cells were seeded in complete medium 48 h prior to uptake experiments. Cells were incubated with indicated doses of NVP-AUY922 (LC Laboratories, Woburn, Mass.) for 24 h and 10 µg/mL trastuzumab (Roche, Basel, Switzerland) for 1 or 24 h prior to addition of radiotracer.

In Vitro Uptake Assay

For baseline uptake in HER2 positive or negative lineages, $3 \times 10^5$ cells were seeded in complete media in 12-well plates (Corning, Tewksbury Mass.) and allowed to recover overnight. Cells were washed twice with serum-free medium and pulsed with 370 KBq in 500 µL serum-free medium for one h. For blocking studies, cells were co-incubated with tracer and 0.5 mg/mL cold unlabeled [$^{19}$F]GE-226[SEQ ID NO 1].

Cells were washed with PBS, trypsinized, neutralized with complete medium and centrifuged. The pellet was washed three times with PBS and lysed in 120 µL RIPA buffer (Sigma-Aldrich). The radioactivity of 100 µL lysate was counted on a Packard Cobra II gamma counter (Perkin Elmer). Radioactivity was normalized to applied radioactivity and protein content, which was determined for each sample by BCA assay (Pierce, Rockford, Ill.).

Western Blots

Cells were lysed in RIPA buffer containing protease and phosphatase inhibitors (from Sigma-Aldrich). Equal amounts of protein (20 μg) were resolved on 4-15% mini-protean TGX gels (Biorad, Hercules, Calif.) and transferred to PVDF membranes (Trans-Blot Turbo Transfer Packs, Biorad). Membranes were blocked for 1 h in 5% milk in Tris-buffered saline containing 0.1% v/v tween (TBST, Cell Signaling, Danvers, Mass.) and incubated with antibodies against HER2 (Cell Signal, Cat. Nr: 2165 for visualization of p95HER2 and full-length HER2 bands and Cat. Nr: 4290 for blots where only full-length HER2 is shown), EGFR (Cell Signal, Cat. Nr: 4267) or β-actin (Abcam, Cambridge, United Kingdom, Cat. Nr: ab6276) overnight at 4° C. Secondary HRP-conjugated mouse and rabbit antibodies (Santa Cruz Biotechnology, Dallas, Tex.) were applied for one h at room temperature. Signals were visualized using Amersham ECL™ Western Blotting Detection Reagent (GE Healthcare) and Amersham Hyper-film (GE Healthcare).

Small Animal Experimental Models for PET

All animal experiments were conducted by licensed investigators in accordance with the United Kingdom Home Office Guidance on the Operation of The Animals (Scientific Procedures) Act 1986 Amendment Regulations 2012 and within the published guidelines for the welfare and use of animals in cancer research (18). The in vivo experimental models were established in female BALB/c nude mice aged 6-8 weeks (Harlan, Indianapolis, Ind.). For all but SKOV-3 xenografts, mice were subcutaneously (s.c.) implanted with 0.72 mg/60 day release estradiol pellets (Innovative Research of America, Sarasota, Fla.) approximately 2 days before cell inoculation. Xenografts were established by s.c. injection of 100 μL MCF7-vector, MCF7-p95HER2 and MCF7-HER2 cells ($1.5 \times 10^7$ cells in PBS mixed 1:1 with Matrigel™, BD Biosciences, San Jose, Calif.), MDA-MB-361 cells ($5 \times 10^6$ cells in PBS mixed 1:1 with Matrigel™) or SKOV-3 cells ($5 \times 10^6$ cells in PBS) on the back of mice. Tumor dimensions were measured frequently by caliper measurements and tumor volumes calculated by the following equation: volume $mm^3 = (\pi/6) \times a \times b \times c$, where a, b, and c represent 3 orthogonal axes of the tumor. When tumor volumes reached approximately 50-100 $mm^3$ (MCF7 models ~4 weeks post injection, MDA-MB-361 xenografts ~3 weeks post injection and SKOV-3 xenografts ~6 weeks post injection), mice were used for biodistribution or PET imaging studies.

For blocking studies, SKOV-3 xenograft bearing mice were administered 500 μg (~25 mg/kg) cold [$^{19}$F]GE-226 [SEQ ID NO 1] intravenously (i.v.) through the tail vain 20 minutes before administration of radiotracer. To assess interaction of radiotracer with trastuzumab, SKOV-3 xenograft-bearing mice were treated with 50 mg/kg trastuzumab intraperitoneally (i.p.) 2 h prior to the scan. Animals were recovered, treated twice more with 25 mg/kg trastuzumab i.p. and re-scanned 7 days after initial dose. To investigate response to HSP90 inhibition, SKOV-3 xenograft-bearing mice were treated with 50 mg/kg NVP-AUY922 or equivalent volume of vehicle (~5 μL/g body weight; 10% DMSO and 5% Tween-20 in PBS) q.d. i.p. for three days. 24 h after the last treatment, animals were used for PET imaging.

PET-CT Imaging

Mice were anesthetized through isoflurane inhalation and scanned on a dedicated small animal PET-CT scanner (Siemens Multimodality Inveon, Erlangen, Germany). Low dose CT scans were first acquired (80 kVp, 0.5 mA, 220 degree rotation, 600 ms per degree exposure time, 80 μm reconstruction pixel size) for PET attenuation correction and to obtain an anatomical reference. PET images were acquired following a bolus i.v. injection of approximately 3.7 MBq [$^{18}$F]GE-226 in the tail vein. Dynamic emission scans were acquired in list mode format over 60 minutes. The acquired data were sorted into 0.5-mm sinogram bins and 19 time frames for image reconstruction by filtered back projection ($4 \times 15$ seconds and $4 \times 60$ seconds followed by $11 \times 300$ seconds). The Siemens Inveon Research Workplace software was used for visualization of radiotracer uptake. 30 to 60-minute cumulative images of the dynamic data were employed to define 3-dimensional (3D) regions of interest (ROI). Arterial input function was estimated by drawing ROIs over the center of the heart cavity using 0.25 to 2 minutes of cumulative images. The count densities were averaged for all ROIs at each time point to obtain time versus radioactivity curves (TAC). Tumor TACs were normalized to injected dose measured by a VDC-304 dose calibrator (Veenstra Instruments, Joure, Netherlands) and normalized uptake was expressed as percentage injected dose per mL tissue (NUV; % ID/mL). Normalized uptake of radiotracer at 60 minutes ($NUV_{60}$) was used for comparisons. For qualitative image visualization, cumulative images of the dynamic data (30 to 60 min) were also iteratively reconstructed (OSEM3D).

Biodistribution

Tumor-bearing BALB/c nude mice were administered ~3.7 MBq of [$^{18}$F]GE-226[SEQ ID NO 1] i.v. through the tail vein. Mice were sacrificed at different time points by exsanguination. Tissues were excised, weighed and radioactivity counted using a Packard Cobra II gamma counter (Perkin Elmer) and decay corrected. Data were expressed as percent injected dose per gram of tissue (% ID/g).

Metabolic Stability

Mice were administered 3.7 MBq [$^{18}$F]GE-226[SEQ ID NO 1] i.v. through the tail vein. At 10, 30 and 60 minute post injection, mice were exsanguinated via cardiac puncture and blood removed for centrifugation. Plasma was obtained and kept on ice for analysis of radioactive metabolites by HPLC.

Small Animal Models for Fluorescent GE-226 Experiments

The bilateral A431/NCI-N87 model was established by s.c. injection of A431 ($1 \times 10^7$ cells) and NCI-N87 cells ($2 \times 10^6$ cells) in 100 μL PBS mixed 1:1 with Matrigel™ in the lower flanks of 4-6 week old male CD-1 nude mice (Charles River Laboratories, Wilmington, Mass.). Tumor volumes were monitored frequently as described above and when they reached 50-100 $mm^3$ (approximately 3-4 weeks), mice were administered a mixture of Hoechst (~20 mg/kg) and fluorescein-conjugated-GE226[SEQ ID NO 1] (~15 mg/kg) in 100 μL PBS i.v. through the tail vein. The tumors were excised 120 minutes post injection, immediately fixed in formalin and embedded in paraffin. Sections were sliced and stored in the dark at −80° C. Immunofluorescent images were acquired at 400× magnification. Adjacent tumor sections were immunohistochemically stained with HercepTest™.

Immunohistochemistry

HER2 protein expression in excised tumors was assessed using the HercepTest™ (Dako, Ely, United Kingdom, Cat. Nr: K5204) according to manufacturer's instructions.

Elisa

Excised and snap frozen tumor tissue samples were homogenized in RIPA lysis buffer (Sigma-Aldrich) with the PreCellys 24 homogenizer and CK14 beads-containing tubes (two cycles of 25 seconds at 6500 rpm). HER2 expression was determined by ELISA (Calbiochem, Darmstadt, Germany, c-ErbB2/c-Neu Rapid Format ELISA Kit, Cat. Nr: QIA10-1EA) according to manufacturer's instructions.

Kinetic Modeling

Kinetic analysis of PET data was performed applying a standard two-tissue irreversible compartmental model to fit each tumor TAC with the corresponding image-derived plasma TAC as input function (IF) to estimate $K_1$ (mL/cm$^3$/min), $k_2$, (1/min) and $k_3$ (1/min) and the blood vascular component $V_b$ (mL blood/mL tissue; unitless). The irreversible uptake rate $K_i$ (mL/cm$^3$/min) was computed as $K_1 \times k_3 / (k_2 + k_3)$. To estimate the kinetic parameters the measured tumor TAC (tTAC) was modeled as $$tTAC(t) = (1 - V_b)h(t) \otimes IF(t) + V_b IF(t)$$

with h(t) indicating the unknown tissue impulse function and $\otimes$ the convolution operator. The parameter vector $p = [K_1, k_2, k_3, V_b]$ was estimated with the standard Weighted Non-Linear Least Squares (WNLLS) by minimizing the Weighted Residual Sum of Squares (WRSS) function $$WRSS(p) = \sum_{i=1}^{N} w_i [tTAC(t_i, p)^{MODEL} - tTAC(t_i)]^2$$

with $tTAC(t_i)$ and $t_i$ indicating the measured concentration in the tumor and mid-time of i-th frame, respectively, and N denoting numbers of frames. Weights were set to $$\frac{\Delta_i}{C(t_i) \exp(\lambda t_i)}$$

with $\Delta_i$ and $\lambda$ representing the duration of the i-th frame and decay-constant of $^{18}$F (19). The two-tissue irreversible model was chosen after visual assessment of the tumor TACs, which showed clear irreversible uptake in most cases. Furthermore, when a two-tissue reversible compartment model was used, non-physiological estimates of the parameters characterized by high variance were obtained.

Statistical Analysis

Data were expressed as mean±standard deviation (SD) or standard error of the mean (SEM). The significance of comparison between two data sets was determined using unpaired, two-tailed Student's t test (GraphPad Prism version 5.1) and P<0.05 defined as significant.

Affibody-HER2 Binding Properties

To ensure the fluorinated prosthetic group does not adversely influence the Affibody binding kinetics, the receptor interaction of the $^{19}$F-Affibody analogue was measured using surface plasmon resonance and compared this to binding of human full-length and truncated p95HER2, as well as rhesus and rat full-length HER2. While the tracer showed very strong binding to human ($K_D$=76 pM) and rhesus HER2 ($K_D$=67 pM), it did not interact with p95HER2 or rat HER2 (Table 1, FIGS. 6A-6D).

[$^{18}$F]GE-226 Exhibits Specific and Lineage-Independent HER2 Binding

The tracer retention was tested in 10 different cell lines derived from breast, upper gastrointestinal tract and ovarian cancer, of which half were HER2 negative and the other half HER2 positive. The panel included an isogenic model comprising of HER2 negative MCF7 cells, which were transfected with empty vector (MCF7-vector), p95HER2 (MCF7-p95HER2) or full-length HER2 (MCF7-HER2).

Figure 7:
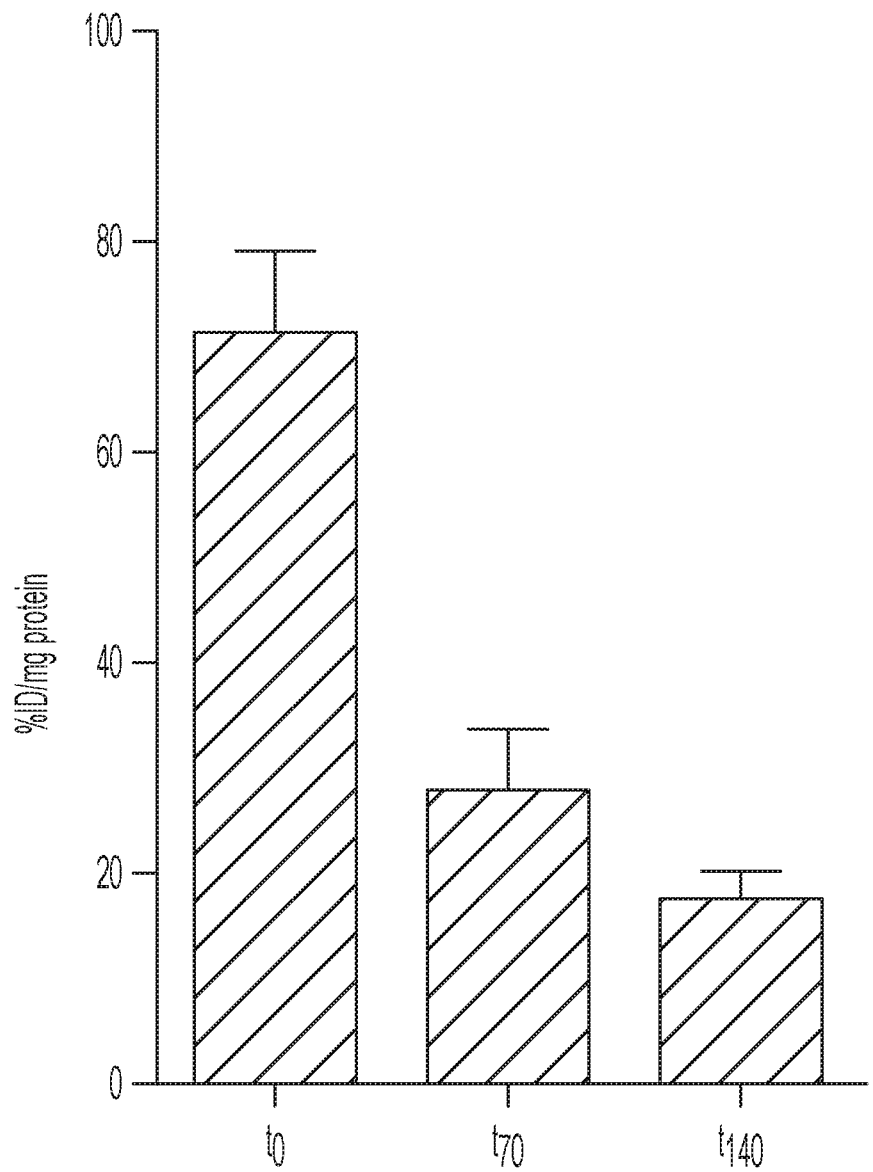
FIG. 7 shows tracer uptake is dependent on specific activity. SKOV-3 cells were pulsed with 20 µCi/mL [$^{18}$F]GE-226[SEQ ID NO 1] either immediately upon receipt of tracer (to), 70 min (t70) or 140 min (t140) after first incubation and cell-bound radioactivity measured. N=1 in at least duplicate. Error: SD.

While all HER2 negative and p95HER2 transfected cell lines had only marginal background uptake (1.2±0.5% applied radioactivity per mg protein across all lines), all HER2 positive cell lines retained the tracer at high levels (between 13.6±3.4 and 79.9±12.1% applied radioactivity per mg protein) and in good agreement with endogenous HER2 expression. Tracer binding was, however, independent of expression of another epidermal growth factor receptor family members, EGFR. FIG. 1A shows one representative uptake experiment, as initial experiments revealed that the uptake was strongly dependent on the specific activity. In comparison to freshly prepared [$^{18}$F]GE-226, the same radiotracer preparation yielded only 39.5±8.5 and 24.9±3.8% tracer uptake if incubation was initiated 70 and 140 minutes later (FIG. 7).

Figure 1B:
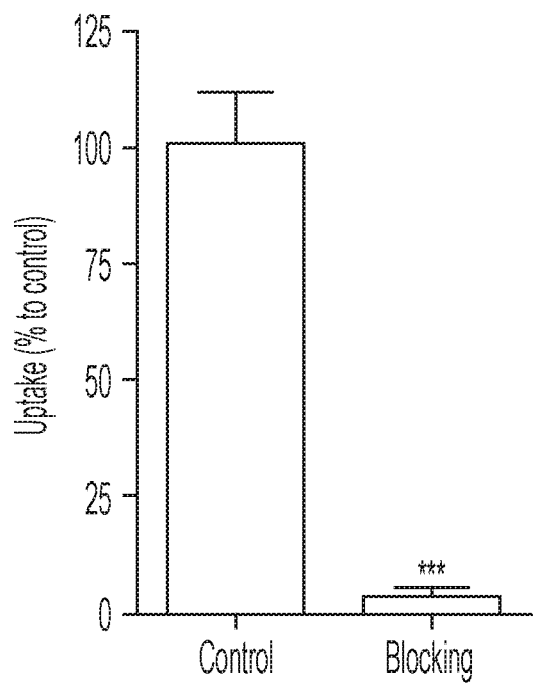
Figure 1C:
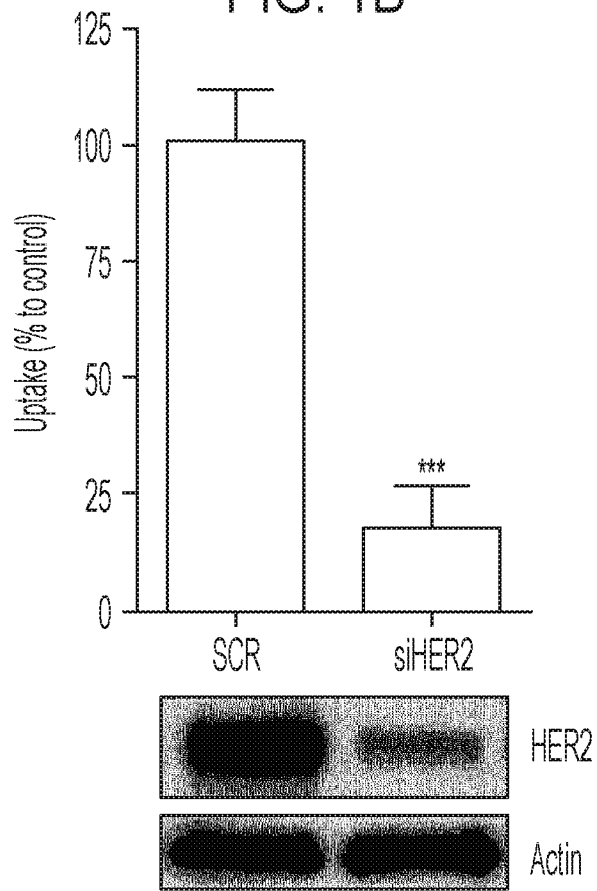

To further investigate the specificity of the signal, SKOV-3 cells were co-incubated with tracer and large excess of its non-radioactive $^{19}$F analogue (FIG. 1B). This reduced uptake to 3.1±2.6% compared to control cells (100±12%; P<0.0001). Furthermore, transient siRNA-mediated knockdown of HER2 decreased tracer uptake compared to non-targeting scramble control (FIG. 1C, 100±12% versus 18±9%, P<0.0001). Target knockdown was confirmed by western blot.

[$^{18}$F]GE-226 exhibits a different binding site than trastuzumab and predicts detection of HER2 degradation by NVP-AUY922

Figures 2A, 2B:
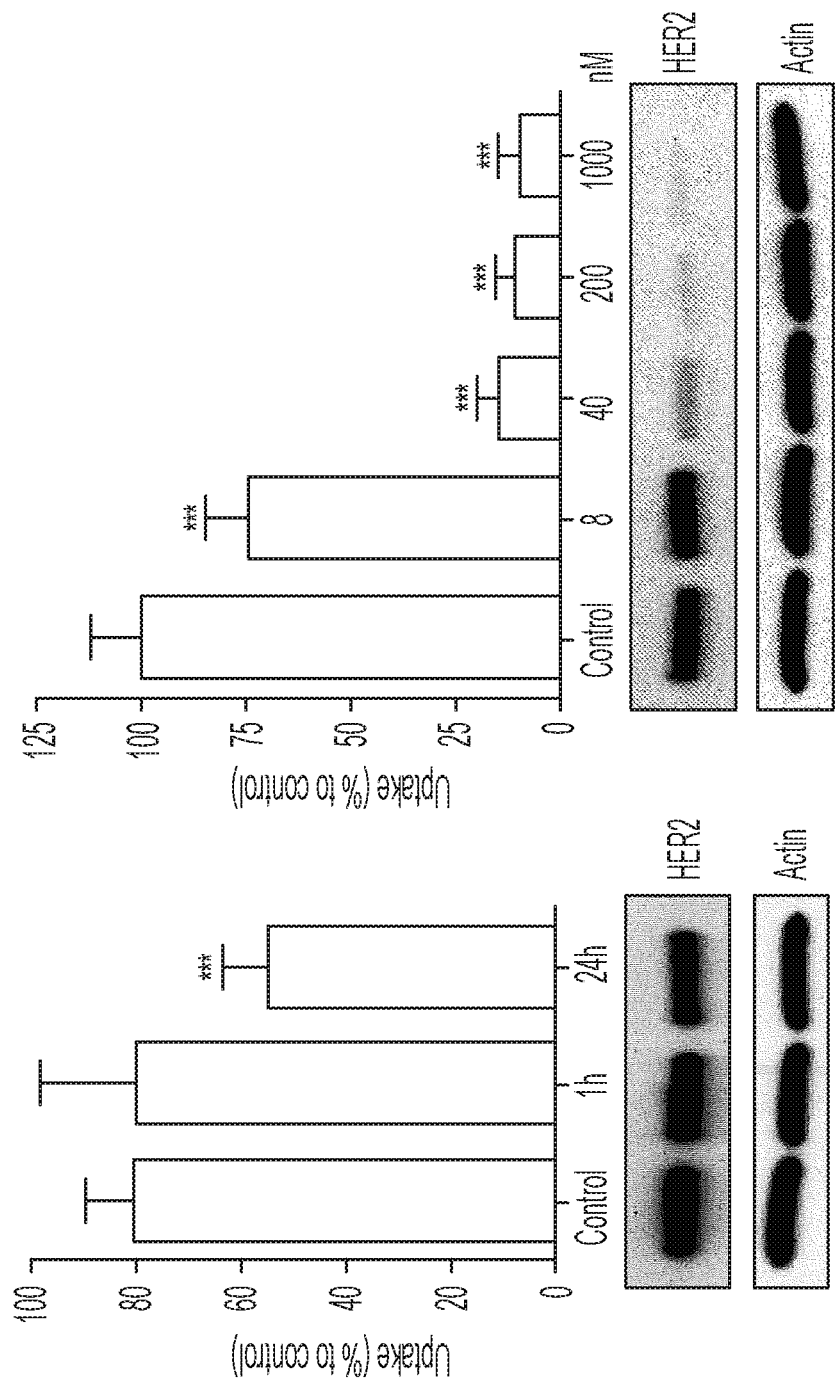
FIGS. 2A-2B shows [$^{18}$F]GE-226[SEQ ID NO 1] possesses a different binding site than trastuzumab and detects HER2 degradation upon HSP90 inhibition: (2A) SKOV-3 cells were treated with 10 µg/mL trastuzumab for 1 or 24 h and incubated for an additional h with [$^{18}$F]GE-226[SEQ ID NO 1] and retained activity compared to untreated controls (*** P<0.0001; mean of n=5 in triplicate on five different days±SD). Effect on HER2 protein expression is shown in the panel below, (2B) Effect of HSP90 inhibitor NVP-AUY922 on HER2 expression and consequent impact on tracer uptake (P<0.0001 for all concentrations compared to control; mean of n=3 in triplicate on three different days±SD).

An important question when developing a HER2-targeting imaging probe is whether the tracer can correctly determine the HER2 status of a patient independently of potential trastuzumab treatment. Pre-treatment of SKOV-3 cells with 10 μg/mL trastuzumab for 1 h did not alter tracer binding, however, incubation for 24 h prior to uptake experiment reduced tracer binding by 32±11% compared to drug-naïve controls (FIG. 2A; P<0.0001).

It is hypothesized that HER2 degradation consequent to HSP90 inhibition (HER2 is a client protein of HSP90 (20)) would result in detectable changes in tracer uptake. The HSP90 inhibitor NVP-AUY922 caused a dose-dependent decrease of HER2 protein expression compared to untreated controls, which consequently translated into reduced tracer uptake, further supporting its specificity (FIG. 2B; P<0.0001 for all tested concentrations compared to control).

Figure 3A:
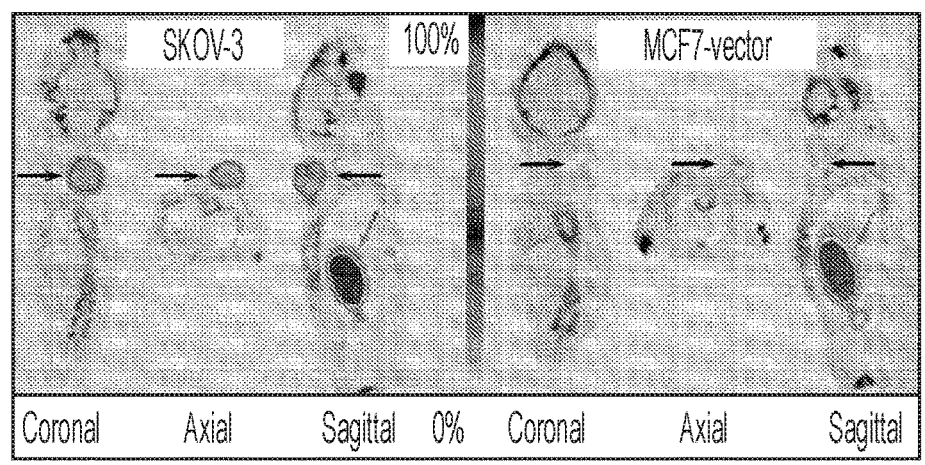
FIGS. 3A-3D shows tumor profiles of [$^{18}$F]GE-226[SEQ ID NO 1] in differentially HER2 expressing xenograft models: (3A) Representative OSEM3D reconstructed PET-CT images of SKOV-3 xenograft-bearing mice. Dark arrow indicates tumor, light arrow kidney, (3B) Comparison of tumor time versus radioactivity curves in indicated xenograft models (mean of n=6±SEM with exception of MCF7-p95HER2 n=3±SEM), (3C) Correlation between NUV60 and HER2 expression as determined by ELISA on tumor lysates, (3D) Tissue pharmacokinetic analysis using a single input 2-tissue 3 k model to derive Ki, the rate constant for the net irreversible retention of the tracer in the tumor.
Figure 3B:
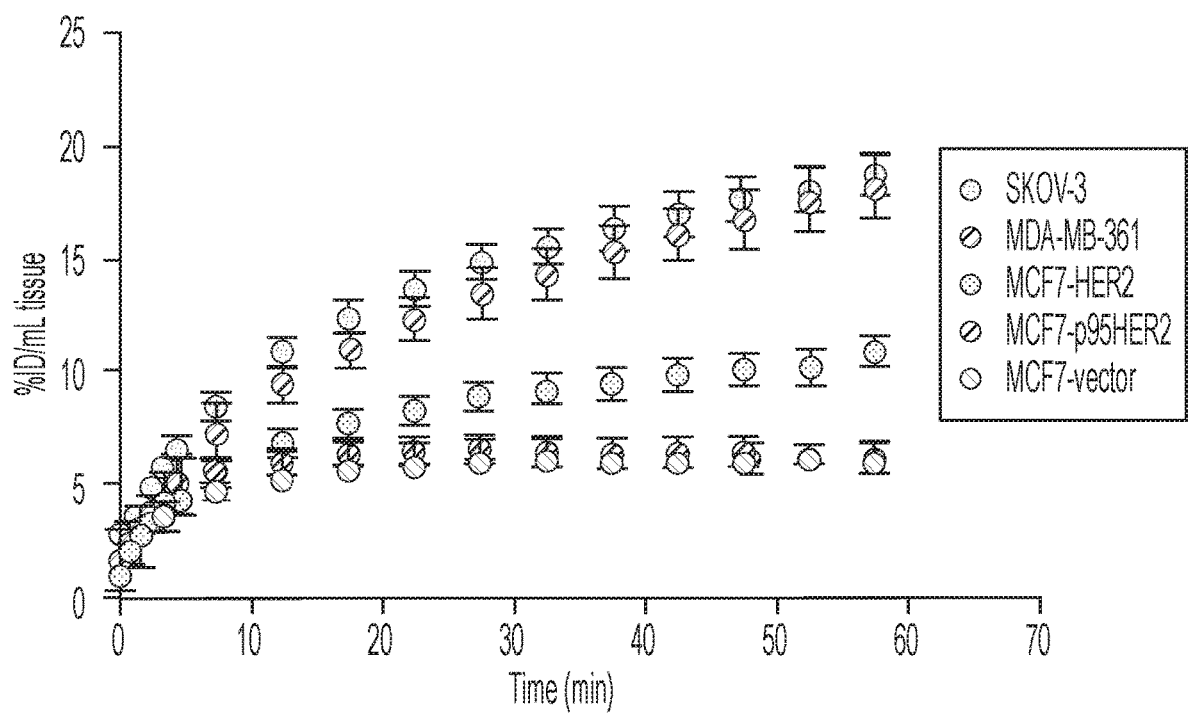
Figure 3C:
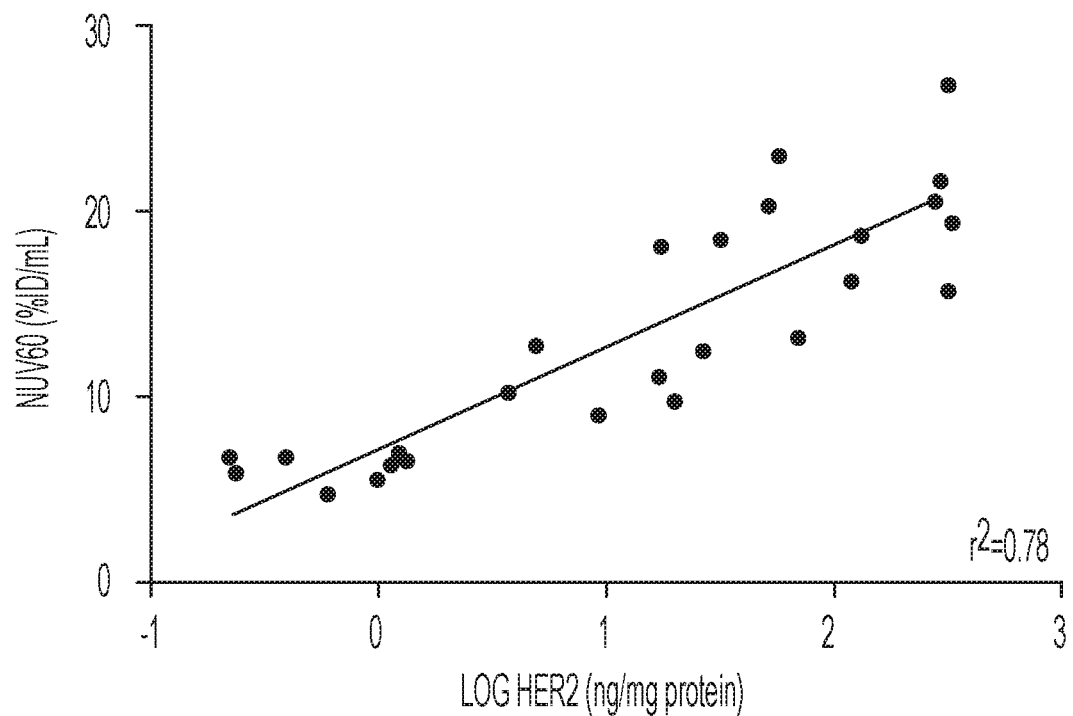
Figure 8A:
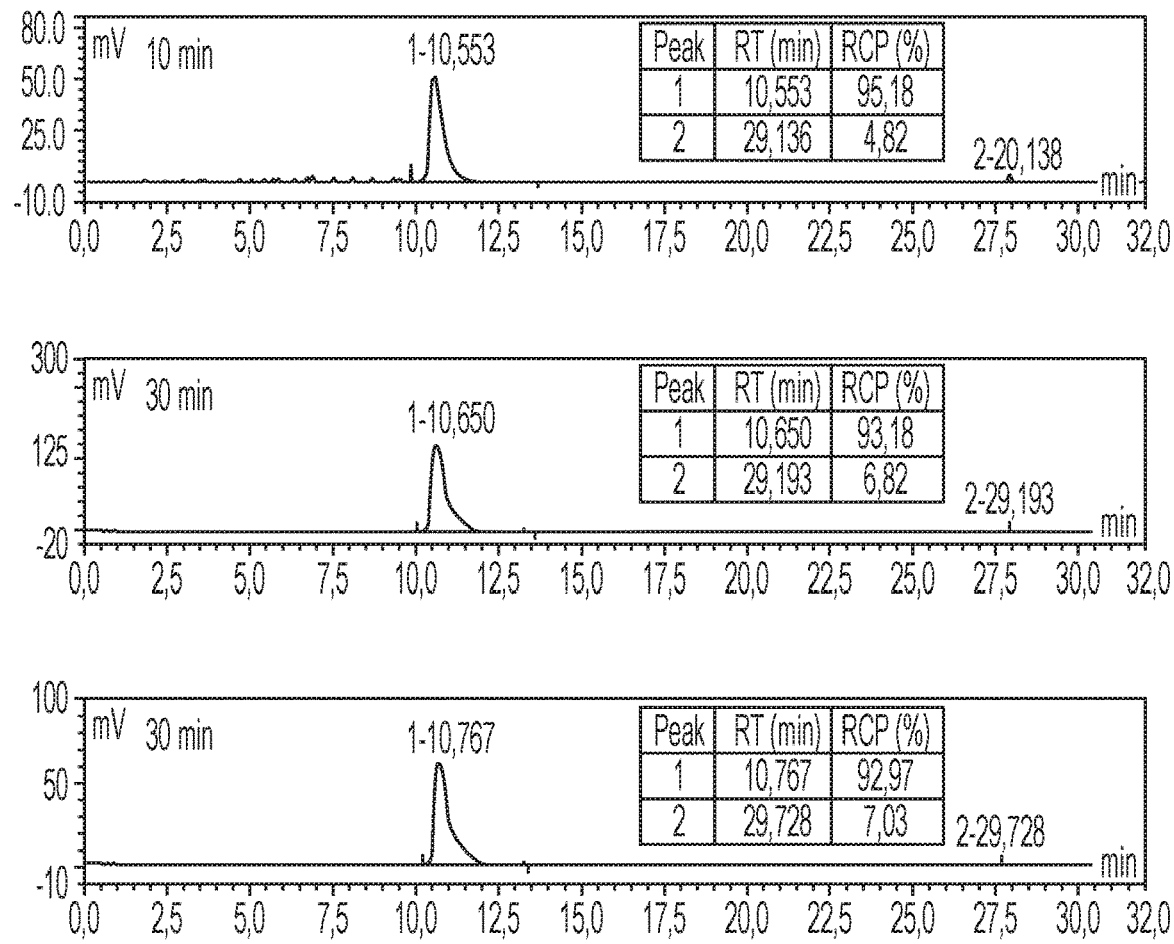
FIGS. 8A-8B show mice were administered 3.7 MBq [$^{18}$F]GE-226 [SEQ ID NO 1] i.v. and metabolites quantified by radio-HPCL 10, 30 and 60 minutes post injection. Metabolic stability was assessed by comparison of parent peak (retention time (RT)—10.6 minutes) with metabolites (RT-29 minutes) and is represented as percent radiochemical purity (RCP), and time versus radioactivity curves derived from PET data for uptake in heart, tumor and kidneys in SKOV-3 xenograft bearing mice (n=6).
Figure 8B:
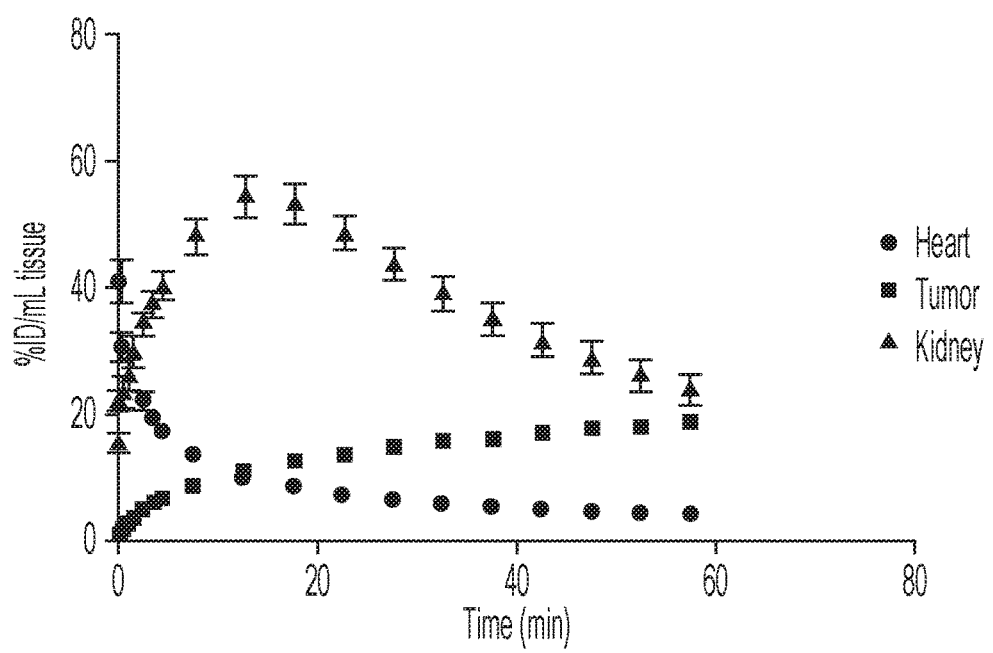
Figure 9A:
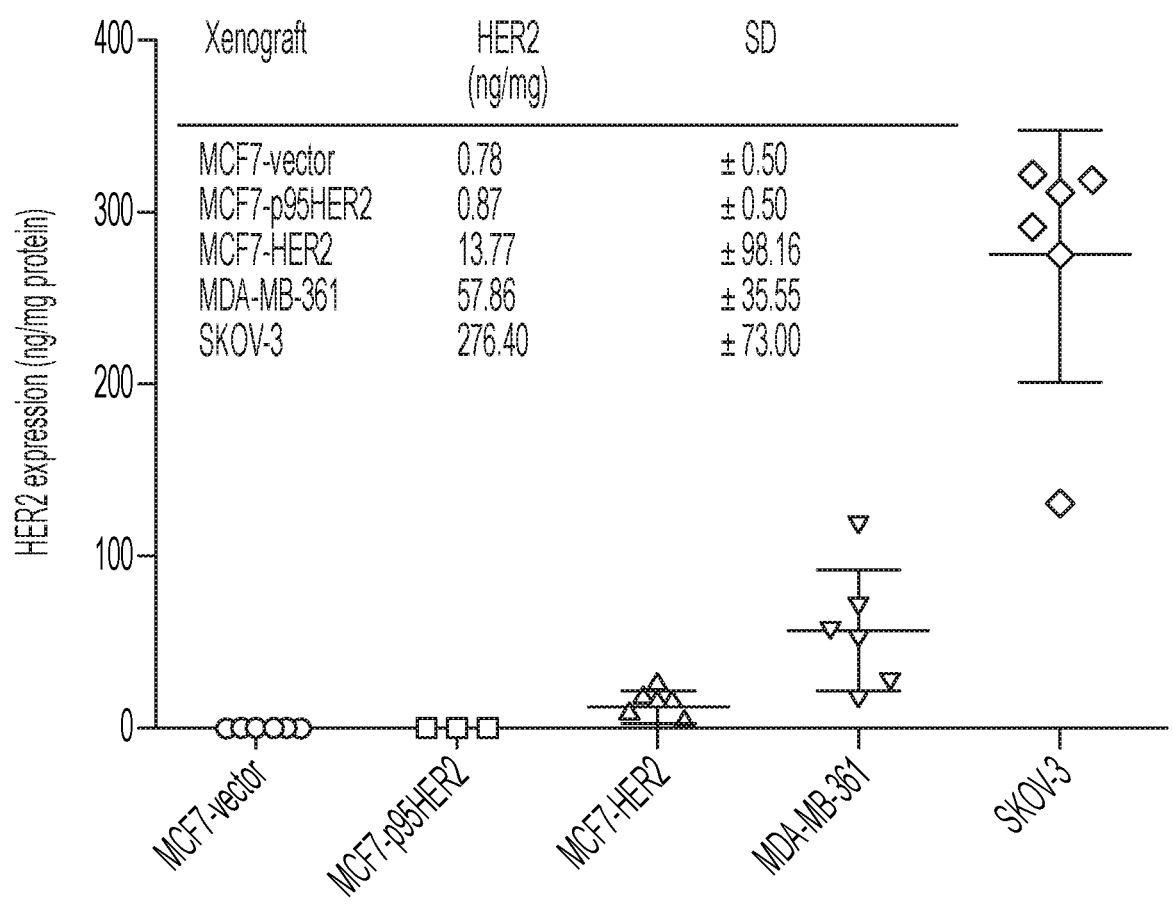
FIGS. 9A-9B show HER2 expression in various xenograft models as determined by ELISA and Kinetic parameters of [18F]GE-226[SEQ ID NO 1] binding in these xenografts.
Figure 9B:
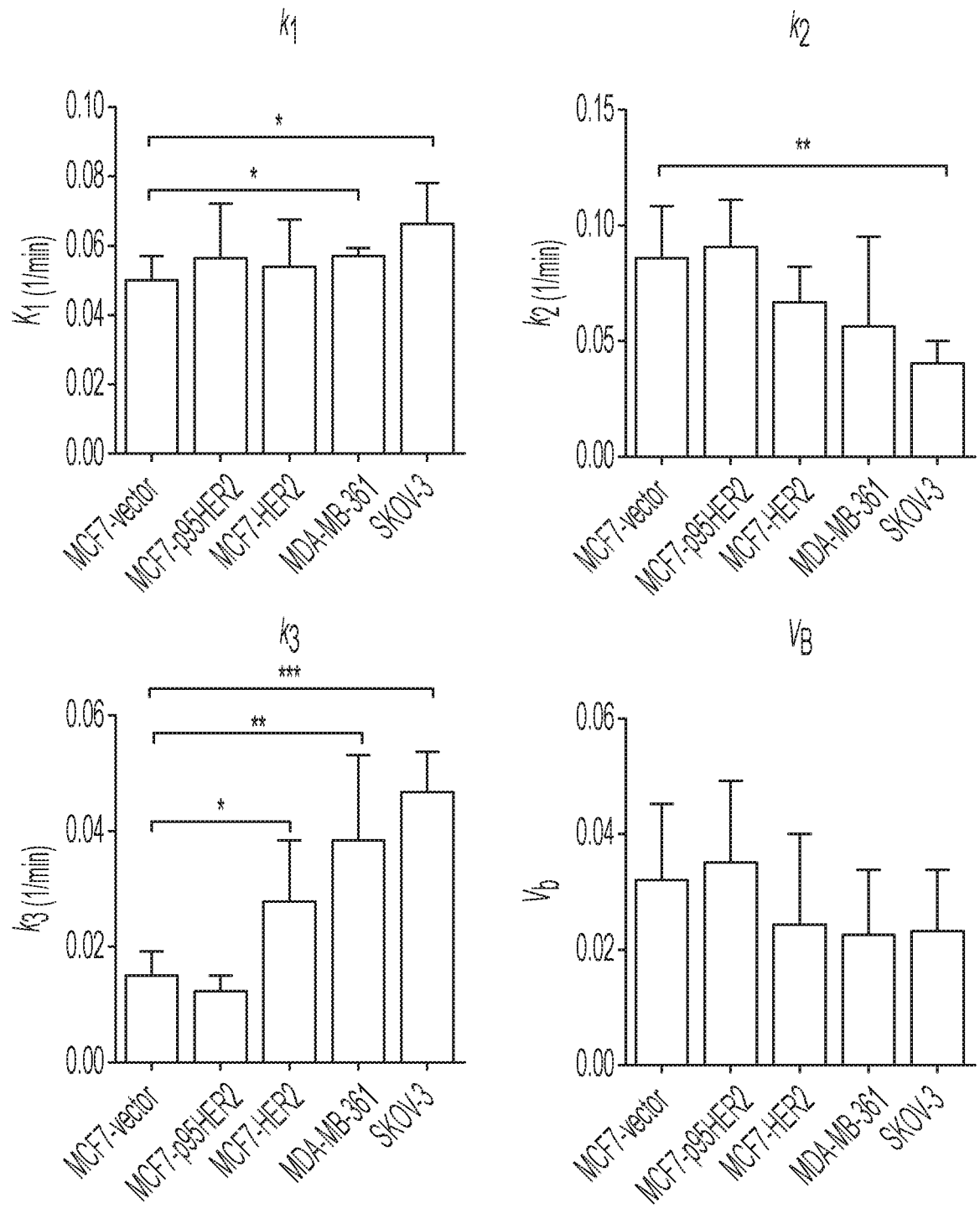
Figure 10B:
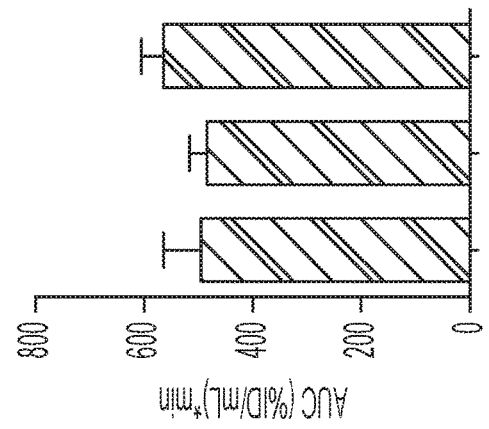
FIGS. 10A-10B show TACs and $AUC_{0-60}$ for uptake in heart (10A, 10B) and kidney (10C, 10D) of drug-naïve or trastuzumab-treated SKOV-3 xenograft bearing mice (***P=0.0004).
Figure 10D:
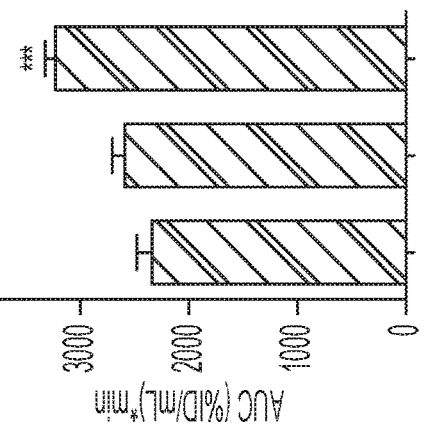
Figure 10A:
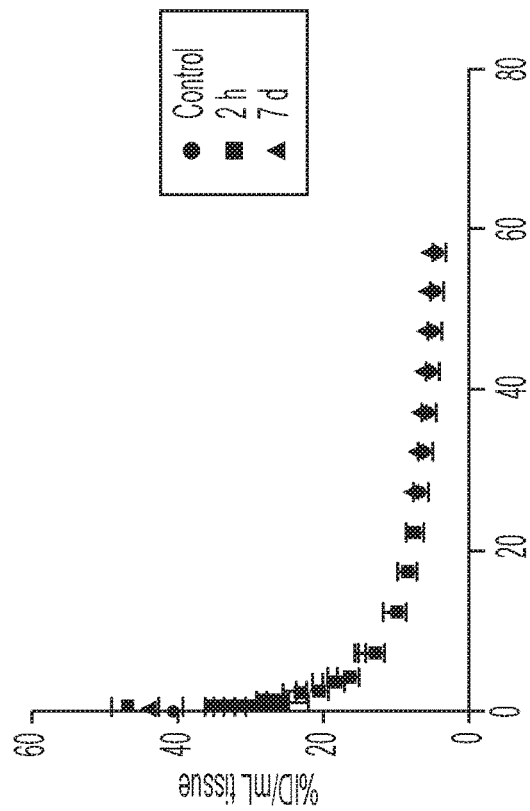
Figure 10C:
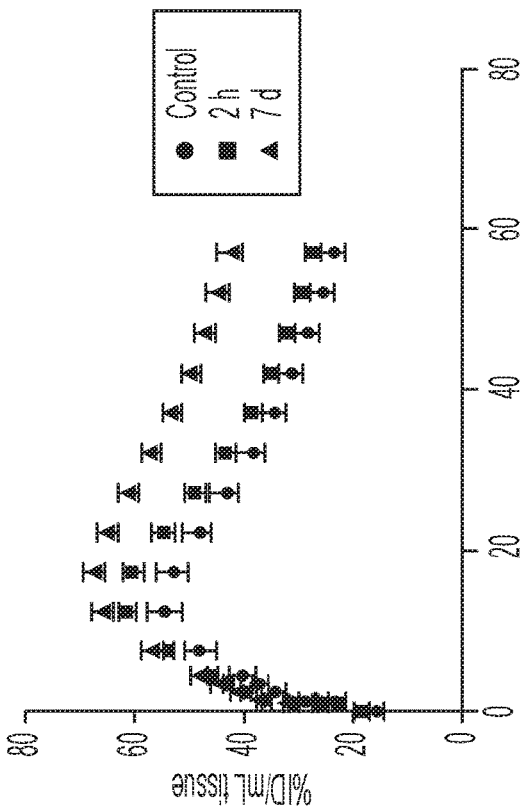

[$^{18}$F]GE-226[SEQ ID NO 1] Discriminates Differential HER2 Expression In Vivo Based on the in vitro data, it was desired to scrutinize the ability of the tracer to distinguish varying degrees of HER2 expression in the complex tumor milieu in vivo. FIG. 3A shows representative small-animal [$^{18}$F]GE-226[SEQ ID NO 1] PET images of a SKOV-3 xenograft-bearing mouse. High tumor uptake contrasts the low non-specific retention in the body. The tracer was metabolically stable and predominately and rapidly excreted via the renal route (FIGS. 8A-8B and Table 2). Across different tumor models, the tracer discriminated well between HER2 positive and negative xenografts. Both tumor-specific distribution and retention kinetics accounted for these differences. While HER2 negative MCF7-vector and MCF7-p95HER2 xenografts exhibited low tumor retention and a steady-state tissue radioactivity after initial delivery, HER2 positive xenografts had increased uptake and followed a pattern of net irreversible binding (FIG. 3B). Thus [$^{18}$F]GE-226[SEQ ID NO 1] PET was able to distinguish HER2-negative (MCF7-vector and MCF7-p95HER2) from low (MCF7-HER2) and moderately (MDA-MB-361) HER2-expressing xenografts. However, tissue radioactivity was comparable in tumors with moderate and highly (SKOV-3) HER2-expression when simple measures of uptake were employed for PET analysis. Nonetheless, radiotracer uptake correlated well with HER2 protein expression as determined by ELISA ($r^2$=0.78; FIG. 3C and FIGS. 9A-9B).

Figure 3D:
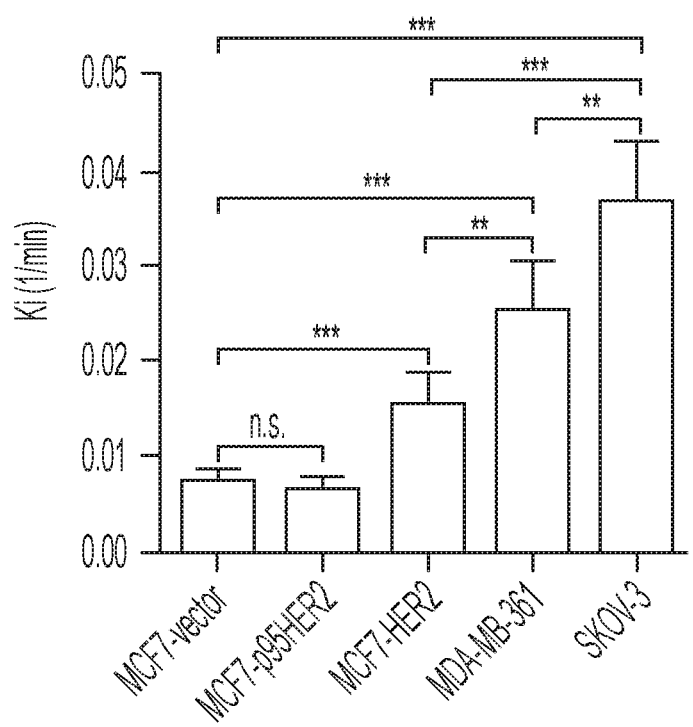

It was hypothesized that kinetic modeling, which accounts for tissue uptake relative to plasma as opposed to tissue uptake alone, could further help discern the various HER2 groups. A two-tissue irreversible compartmental model was employed to derive the net irreversible uptake rate constant, $K_i$ (FIG. 3D). With this model, we could distinguish all groups, even MDA-MB-361 from SKOV-3 xenografts (FIG. 3D). As expected, $K_1$ highly correlated with $NUV_{60}$ among all groups ($r^2$=0.82; P=0.008).

To lend further support to the specificity of the Affibody, we carried out blocking studies by injecting 30 mg/kg [$^{19}$F]GE-226 i.v. 20 minutes prior to PET scan (~1000 fold of the radiolabelled tracer). SKOV-3 zeongraft bearing mice were treated with 30 mg/kg [19F]GE-226 in PBS i.v. 20 minutes before PET scan compred to untreated controls. The cold ligand, by blocking specific binding sites, resulted in significantly reduced tracer uptake ($NUV_{60}$ 18.7±2.4 versus 7.1±1.6 in controls and blocked tumors, P=0.0003) and $K_1$. It is noteworthy that the kinetics of tracer uptake were distinctly different between controls and blocked samples, in that the latter share characteristics of HER2 negative tumors. Localization and Intensity of Fluorescent GE-226 Correlates with DAKO HercepTest™

Figure 4:
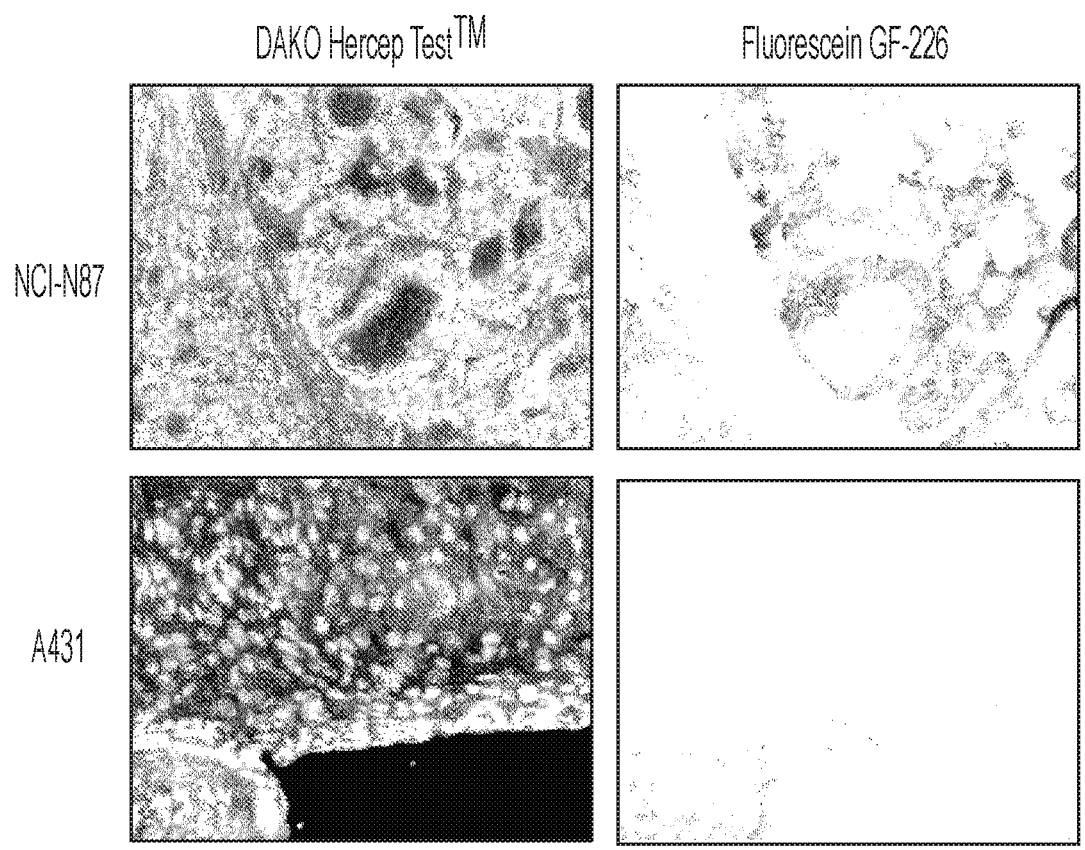
FIG. 4 shows GE-226[SEQ ID NO 1] co-localizes with HER2 protein expression in tumors with special heterogeneity. GE-226[SEQ ID NO 1] was labeled with fluorescein and injected in mice bearing both NCI-N87 and A431 tumors, which express high and low levels of HER2, respectively. Tumors were sectioned and adjacent slides either stained with DAKO HercepTest1M or used for immunofluorscent microscopy.
Figure 6A:
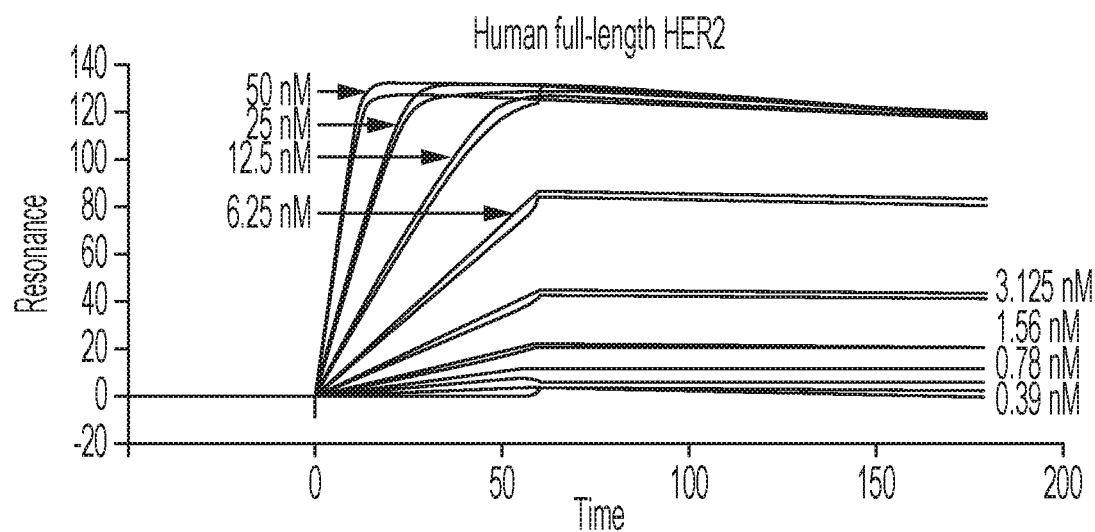
FIGS. 6A-6B show GE-226 [SEQ ID NO 1] binds with high affinity to human (6A) and rhesus (6B) HER2, but not to human p95HER2 (6C) or rat HER2 (6D), as determined by Surface Plasmon Resonance.
Figure 6B:
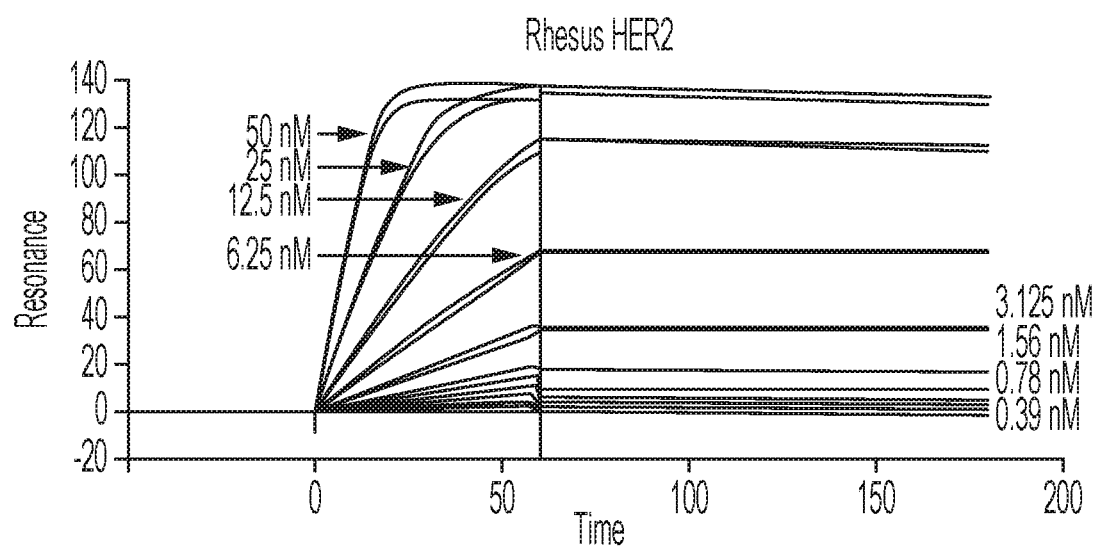
Figure 6C:
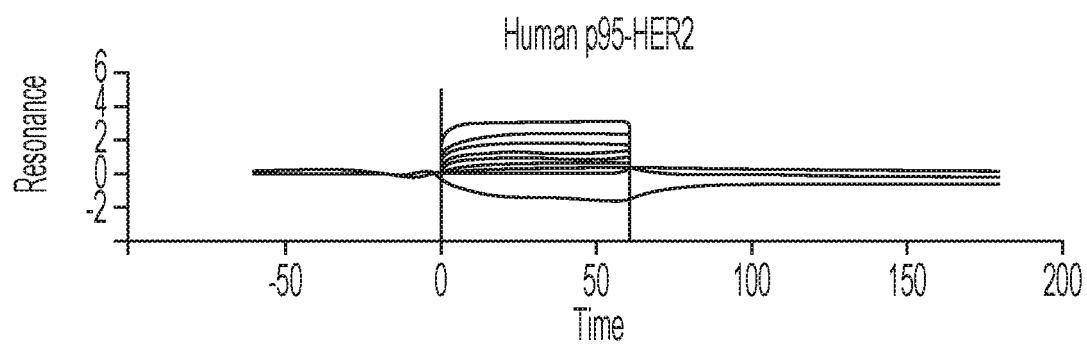
Figure 6D:
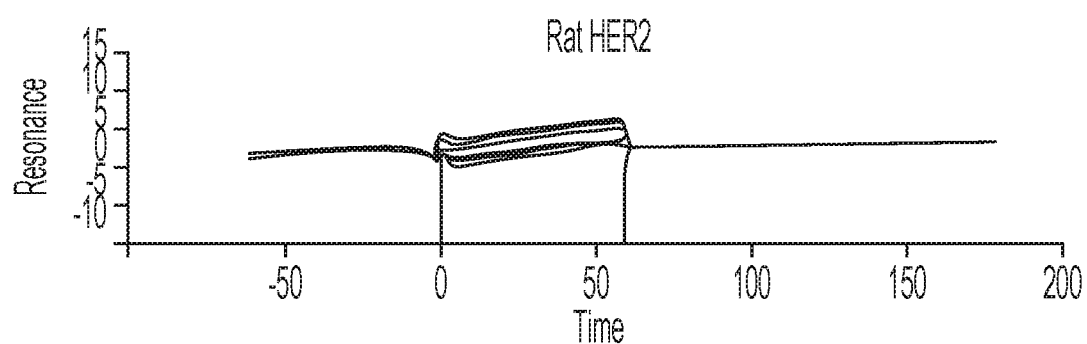

To examine cellular localization, GE-226[SEQ ID NO 1] was labeled with fluorescein and compared localization and fluorescent intensity in tumor sections with FDA approved DAKO HercepTest™. In contrast to PET experiments, normalization to injected dose is not possible with fluorescent compounds. To eliminate inter-subject variability, experiments were performed in bilateral tumor-bearing mice. Because HER2 positive and negative xenografts described in FIGS 3A-3C. 3 have greatly varying growth rates and require differential hormonal treatments, we employed A431 (HER2 negative) and NCI-N87 (HER2 positive) xenografts. A mixture of 20 mg/kg Hoechst and 15 mg/kg fluorescein-GE-226 in PBS were injected i.v. and two h post injection, tumors were excised, formalin fixed and paraffin embedded and adjacent tumor sections prepared for HercepTest™ staining or fluorescent microscopy. FIG. 4 shows that fluorescent staining co-localized with regions that are HER2 positive in NCI-N87 tumors and that both HercepTest™ and fluorescent staining in A431 tumors were negligible.

[$^{18}$F]GE-226[SEQ ID NO 1] can correctly assess HER2 status independently of prior trastuzumab treatment and predicts for response to NVP-AUY922 in vivo.

Figure 11:
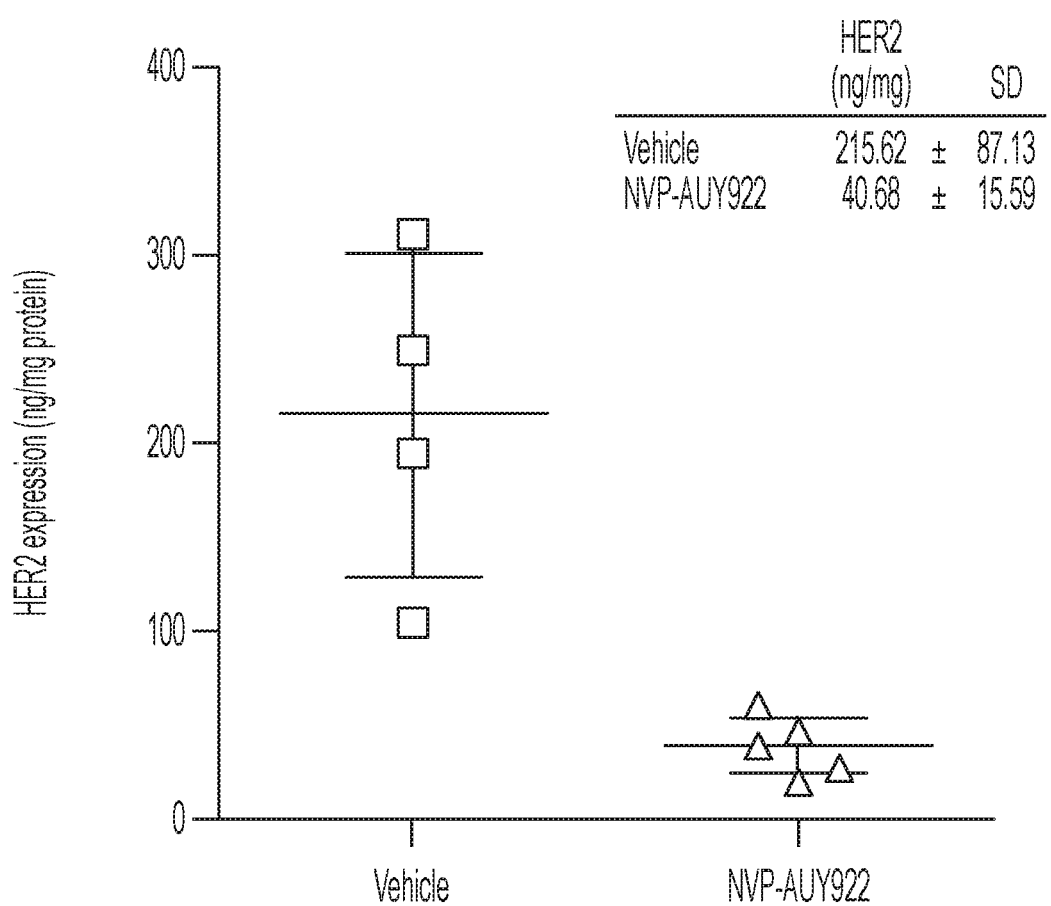
FIG. 11 shows HER2 expression in SKOV-3 tumors after treatment with 3 doses of 50 mg/kg NVP-AUY922 in comparison to vehicle (10% DMSO and 5% Tween-20 in PBS).

SKOV-3 tumor bearing mice were treated with three doses of trastuzumab and imaged 2 h post initial dose and re-imaged 48 h after last treatment (i.e. 7 days after initial scan). Both treatments did not adversely affect tumor tracer retention (FIG. 5A), albeit 7 days of continuous treatment reduced $K_i$ by 24% (P=0.025) as a consequence of elevated arterial input function and altered renal excretion (FIG. 5B, FIGS. 10A-10D). This confirmed that the Affibody possesses different binding sites to trastuzumab. Finally, to assess whether [$^{18}$F]GE-226[SEQ ID NO 1] could also be utilized as response to treatment biomarker for HSP90 inhibition in vivo, SKOV-3 xeongraft bearing mice was treated with 3 doses of 50 mg/kg NVP-AUY922 or vehicle. This led to reduced HER2 expression with consequently decreased tracer uptake (FIGS. 5C-5D, FIG. 11).

With the aid of kinetic modeling, we demonstrate that the $Z_{HER2:2891}$ Affibody, [$^{18}$F]GE-226[SEQ ID NO 1], quantitatively discriminates between HER2 negative and positive tumors within 1 h, independent of lineage and prior treatment with trastuzumab. Affibody radiotracers have been developed to overcome the shortcomings of large (150 kDa) antibodies. To date most of the reported studies of radiolabeled Affibody molecules in the literature have employed analogs of $Z_{HER2:342}$ labeled with radiometals or radiohalogens (16, 21-26). Recently, re-engineering of this Affibody by Feldwisch and co-workers (27) led to an optimized scaffold containing 11 amino acid substitutions in the non-binding surface of the Affibody removing similarity to the original protein A domain—$Z_{HER2:2891}$. Further to potential for automated site-specific GMP-grade manufacture on FASTlab to allow broad clinical access to a HER2 imaging agent, $Z_{HER2:2891}$ has improved thermal and chemical stability by avoiding deamidation, as well as increased hydrophilicity of the non-binding surface; positive attributes for ease of peptide synthesis and in vivo pharmacokinetics. The latter property is desirable to permit conduct of imaging studies within 1-2 h post-radiotracer injection. However, within this early period non-specific uptake could contribute to tissue signal. The specificity of $^{18}$F-radiolabeled $Z_{HER2:2891}$ Affibody, [$^{18}$F]GE-226[SEQ ID NO 1], was assessed for early imaging (1 h) using both intrinsic cellular uptake and in vivo dynamic imaging to quantitatively discriminate between HER2 negative and positive tumors.

Optimization of contrast is pivotal to successful development of imaging agents. High contrast results largely from high affinity of radiotracers and rapid pharmacokinetics. By comparison with other molecular imaging probes, Affibody molecules benefit from a short blood circulation time and high target affinity resulting in high contrast images within a relatively short time after injection, and slower internalization rates (23, 28, 29). This permits utilization of more widely available short-lived radioisotopes, such as $^{18}$F and $^{68}$Ga, minimizing the patient's dosimetry. In comparison with nanobodies, Affibody molecules excel through lower $K_D$, higher $k_{on}$ and slower $k_{off}$ rates (30). Regarding affinity, Surface Plasmon Resonance experiments with the cold unlabeled [$^{19}$F]-GE-226[SEQ ID NO 1] revealed high affinity binding to human and rhesus HER2-ECD-Fc comparable to the binding of parent $Z_{HER2:2891}$ Affibody to human HER2-ECD-Fc (76 pM (27)). In contrast, [$^{19}$F]GE-226[SEQ ID NO 1] did not interact with rat HER2-ECD-Fc or human p95HER2, demonstrating specificity to the ECD-containing human protein. Radiofluoridation to produce [$^{18}$F]GE-226 [SEQ ID NO 1] did not affect radiotracer affinity either, as demonstrated by high specific cell intrinsic uptake in HER2 positive (approximately 11 to 67-fold higher) versus negative human breast, upper-gastrointestinal and ovarian cancer cell lines. Notably the lineage independence observed also lends support to the specificity of the radiotracer for HER2 versus other targets like EGFR and potential utility in cancers other than breast.

Preclinical imaging with $Z_{HER2:2891}$ radiolabeled with $^{111}$In via a DOTA conjugate displays good tumor targeting in SKOV-3 xenografts (28). While large radiohalogens such as $^{125}$I have been reported to affect tumor targeting of Affibody molecules in comparison to $^{111}$In, rather high uptake of [$^{18}$F]GE-226[SEQ ID NO 1] in vivo.was observed. Indeed uptake of [$^{18}$F]GE-226[SEQ ID NO 1] in the high HER2 expressing SKOV-3 tumor at the early timepoint of 1 h (tumor/muscle ratio of ~60) was comparable to that reported for [$^{111}$In]-DOTA-$Z_{HER2:2891}$ (tumor/muscle ratio of ~50). With the superior sensitivity, resolution, and quantification of PET compared to single photon computed emission tomography (SPECT; used for imaging of $^{111}$In radioisotope (28)), it is expected that [$^{18}$F]GE-226[SEQ ID NO 1] will provide superior contrast at the early timepoints compared to analogous [$^{111}$In]-DOTA-Z$_{HER2:2891}$-based SPECT. On the other hand, delayed imaging e.g. 4 h, if appropriate, can lead to substantial increase in contrast for SPECT radiotracers. Studies in SKOV-3 xenografts showed that tumor tracer uptake was higher at 2 h but the increase was not substantial to warrant selection of this timepoint for further evaluation. Regarding systemic tracer disposition, high renal accumulation is characteristic of radiometal tracers due to reabsorption in the proximal tubules (31). In this context previous Affibody molecules labeled with $^{111}$In showed substantial renal localization (28, 29) approximately 10-fold higher than that seen in tumor, precluding imaging of tumors in the region around the kidney, as well as having an impact on dosimetry. In contrast, rapid renal clearance of [$^{18}$F]GE-226 [SEQ ID NO 1], without substantial tracer accumulation in the kidneys was demonstrated; kidney radioactivity levels were comparable to levels in tumors at 60 min (Table 2). Uptake in other organs, including the liver, was negligible and it remains elusive whether previously detected hepatic uptake of other Affibody molecules in the clinical setting is attributed to Affibody disposition or the labeling strategy; clinical advancement of earlier generation Affibody molecules was hampered by high kidney and liver retention, which obstructed the view on proximate metastasis (32). This effect is likely to be at least in part due to loss of radiometal and retention of radioactive ions in the kidney, which has also been observed in pre-clinical models, where kidney radioactivity was >15-fold higher than tumor uptake and over 72 h (33). Bioconjugation of the Affibody molecule with albumin or $^{18}$F radiolabels have been proposed as alternative approaches to avoid tubular reabsorption and permitting rapid glomerular filtration (23, 34, 35). Our findings support the radiohalogen strategy with $^{18}$F as a means to maintain the favorable pharmacokinetic properties of Affibody molecules in vivo.

The specificity of HER2 binding was assessed in vitro and in vivo. Several lines of evidence indicated that the binding of [$^{18}$F]GE-226[SEQ ID NO 1] to HER2 is highly specific: a) the tracer discriminated between HER2 positive and negative cells and tumors including absence or reduced binding to cells expressing mutant p95HER2 protein that lacks the extracellular domain of the HER2 receptor (17) compared to isogenic vector control cells in vitro and in vivo, b) siRNA knockdown of HER2 protein in cells reduced tracer uptake, c) pre-treatment of cells or mice with cold unlabeled [$^{19}$F]GE-226[SEQ ID NO 1] resulted in significant reduction in uptake and d) tumor distribution of fluorescent labeled-GE-226 co-localized with HER2 protein as determined by DAKO HercepTest™. The latter also demonstrated that tumor distribution of Affibody was non-limiting in the heterogeneous tumor models studied. We intimate that the above desirable affinity and pharmacokinetics properties of [$^{18}$F]GE-226[SEQ ID NO 1] together with its HER2 specificity led to very high contrast PET images of [$^{18}$F]GE-226[SEQ ID NO 1] observed in this study. We acknowledge that the high contrast images in this study are perhaps due also in part to the lack of tracer binding to rodent HER2 (FIGS. 6A-6D), nonetheless, it further substantiates the low non-specific binding of [$^{18}$F]GE-226[SEQ ID NO 1] as rodent data for Affibody molecules have been shown to translate well into human imaging profile.

PET imaging demonstrated rapid tracer uptake in HER2 positive xenografts. The dynamics of uptake followed a net irreversible binding kinetics over time, which led to selection of a two-tissue irreversible compartmental model to fit the tumor data; no metabolite correction was necessary as the tracer was stable in vivo (FIG. 8A). The irreversible uptake (over the time of imaging) made it possible to distinguish between HER2 negative (NUV$_{60}$, MCF7 and MCF7-p95HER2: 6.1±0.7% ID/mL) and HER2 positive tumors (NUV$_{60}$MCF7-HER2: 10.9±1.5; MDA-MB-361: 18.2±3.4; SKOV-3: 18.7±2.4% ID/mL) within 1 h. There is paucity of detailed kinetic analysis of Affibody PET data in the early timepoints following tracer injection.

Time versus radioactivity curves revealed steady-state (limited-washout) background uptake in HER2 negative xenografts, which was in keeping with the normal distribution kinetics of these types of peptides within the literature (23, 33, 36). To further investigate this phenomenon kinetic modeling was employed, which highlighted interesting biological characteristics of the tracer-HER2 interaction. In HER2 negative xenografts (e.g., MCF7 and MCF7 p95HER2), uptake was rapid and remained stable over the 60-minute scan period. As wash-out mechanisms are primarily determined by size, tissue retention of Affibody molecules is longer than of small-molecules nonetheless more favorable than full immunoglobulins. Thus, the uptake observed in HER2 negative tumors can be attributed to non-specific background tissue distribution. In contrast, all HER2 positive models showed a continuous increased uptake throughout image acquisition timeframe. We confirmed that the net irreversible trapping of the tracer in tumor was not due to differences in tracer delivery (K$_i$) or blood volume (V$_b$) but rather to specific uptake (k$_3$; FIG. 9B). Tumor uptake correlated with HER2 expression determined by ELISA (r$^2$=0.78 and 0.82, when the variable was NUV$_{60}$ or net irreversible binding constant K$_1$, respectively). We attribute this correlation to specific Affibody-HER2 interaction, and possibly some receptor internalization (23, 28, 29); receptor internalization was not assessed in this study but localization of the fluorescent labeled Affibody in vivo did not suggest substantial internalization within the timeframe of the study. Importantly, kinetic modeling permits definition of a threshold for HER2 positivity (or more precisely determines the irreversible uptake in HER2 positive tumors).

In view of trastuzumab being the most important HER2-targeting therapy, we wanted to ensure that tracer and antibody did not compete for the same extracellular epitope. We confirmed, both in vitro and in vivo, that uptake of [$^{18}$F]GE-226[SEQ ID NO 1] was not obscured by the presence of trastuzumab. Tracer uptake was not influenced by short-term or continuous treatment with trastuzumab in keeping with differential epitope binding. Minor, but significant, decreases in uptake after 24 h pre-treatment with trastuzumab in vitro are more likely related to altered receptor internalization or other dynamics due to the high concentration used (37, 38).

Finally we confirmed that [$^{18}$F]GE-226[SEQ ID NO 1] is suitable as pharmacodynamic marker of HSP90 inhibition. The most promising of these compounds, NVP-AUY922 (39) is currently in Phase II clinical trials and has previously shown to downregulate HER2 expression (40), which was correctly confirmed in vitro and in vivo by [$^{18}$F]GE-226 [SEQ ID NO 1] PET. This is in accordance with the report by Smith-Jones and co-workers who similarly demonstrated that the HSP90 inhibitor, 17-allylaminogeldanamycin, degrades HER2 leading to reduction in the uptake of [$^{68}$Ga]-labeled F(ab')$_2$ fragment of trastuzumab (36).

In conclusion, [$^{18}$F]GE-226[SEQ ID NO 1] PET imaging permits accurate discrimination of HER2 receptor expression, irrespective of tumor heterogeneity, cell lineage, or prior trastuzumab treatment. We expect the tracer to have good safety and dosimetry profiles due to its low nonspecific binding, the use of short-lived radiolabel and its favorable pharmacokinetic properties. These data support the clinical development of this tracer in cancer patients, which is planned.

TABLE 1

Table 1: Summary of binding kinetics of GE-226[SEQ ID NO 1] to human and rhesus HER2.

| Kinetic properties | Human HER2 | Rhesus HER2 |
|---|---|---|
| On-rate $k_{on}$ | $1.73 \times 10^7$ M$^{-1}$s$^{-1}$ | $6.37 \times 10^6$ M$^{-1}$s$^{-1}$ |
| Off-rate $k_{off}$ | $1.31 \times 10^{-3}$ s$^{-1}$ | $4.25 \times 10^{-4}$ s$^{-1}$ |
| Affinity $K_D$ | $7.58 \times 10^{-11}$ M | $6.67 \times 10^{-11}$ M |
| Rmax | 133.5 | 138.1 |
| Chi-Square $\chi^2$ | 0.607 | 1.12 |
| U-value | 3 | 7 |

TABLE 2

Biodistribution of [$^{18}$F]GE-226[SEQ ID NO 1] in tumor-bearing BALB/c nude mice. Tissue uptake is expressed as % ID/g tissue ± SD (n = 3 per time point).

| | 5 min | 15 min | 30 min | 60 min |
|---|---|---|---|---|
| Plasma | 12.71 ± 14.90 | 9.41 ± 3.75 | 4.10 ± 2.23 | 1.76 ± 1.06 |
| Blood | 0.82 ± 0.83 | 2.00 ± 0.75 | 0.53 ± 0.35 | 0.32 ± 0.26 |
| Heart | 3.10 ± 2.83 | 3.52 ± 1.19 | 1.27 ± 0.60 | 0.64 ± 0.40 |
| Lung | 3.90 ± 3.84 | 5.99 ± 2.10 | 3.15 ± 1.84 | 1.81 ± 1.32 |
| Liver | 2.90 ± 2.96 | 4.58 ± 1.77 | 2.27 ± 1.23 | 1.64 ± 1.49 |
| Gallbladder | 3.22 ± 3.29 | 5.10 ± 1.77 | 2.74 ± 1.06 | 3.92 ± 3.29 |
| Stomach full | 1.47 ± 1.85 | 2.68 ± 1.04 | 1.28 ± 0.92 | 0.53 ± 0.29 |
| Stomach empty | 2.02 ± 1.62 | 3.75 ± 1.38 | 1.56 ± 0.86 | 0.86 ± 0.72 |
| Duodenum full | 2.55 ± 2.17 | 4.07 ± 1.48 | 2.87 ± 1.18 | 1.53 ± 0.59 |
| Duodenum empty | 3.21 ± 3.50 | 5.16 ± 2.36 | 2.91 ± 1.27 | 2.29 ± 2.29 |
| Jejunum full | 1.68 ± 1.38 | 2.71 ± 1.01 | 1.73 ± 1.25 | 0.99 ± 0.39 |
| Jejunum empty | 2.48 ± 2.81 | 4.92 ± 1.33 | 1.87 ± 1.12 | 0.86 ± 0.46 |
| Caecum full | 0.97 ± 1.09 | 1.68 ± 0.85 | 0.60 ± 0.27 | 0.36 ± 0.22 |
| Caecum empty | 3.24 ± 3.76 | 4.94 ± 2.84 | 1.92 ± 0.89 | 0.87 ± 0.53 |
| Colon full | 2.40 ± 2.53 | 3.43 ± 1.89 | 1.00 ± 0.59 | 0.84 ± 0.59 |
| Colon empty | 2.68 ± 2.44 | 5.78 ± 2.99 | 1.80 ± 0.94 | 1.25 ± 0.94 |
| Spleen | 3.18 ± 2.66 | 3.94 ± 3.24 | 1.71 ± 0.90 | 0.88 ± 0.56 |
| Kidney | 15.02 ± 6.99 | 65.82 ± 18.48 | 23.54 ± 11.70 | 11.94 ± 10.30 |
| Muscle | 0.88 ± 0.81 | 2.05 ± 0.86 | 0.78 ± 0.48 | 0.50 ± 0.45 |
| Bone | 1.20 ± 1.08 | 3.05 ± 0.88 | 1.59 ± 0.94 | 0.68 ± 0.40 |
| Brain | 0.33 ± 0.35 | 0.34 ± 0.11 | 0.13 ± 0.08 | 0.10 ± 0.07 |
| Urine | 148.33 ± 127.65 | 283.73 ± 243.00 | 438.65 ± 219.01 | 535.62 ± 303.04 |
| MCF7-vector | | | | 6.76 ± 1.01 |
| MCF7-p95HER2 | | | | 6.55 ± 0.13 |
| MCF7-HER2 | | | | 11.06 ± 3.31 |
| MDA-MB-361 | | | | 17.00 ± 2.98 |
| SKOV-3 | | | | 17.35 ± 0.83 |

What is claimed is:

1. A method of monitoring a dose dependent response HSP90 inhibition, the method comprising:
   (a) administering [$^{18}$F]GE-226 (SEQ ID NO 1) to a HER2 bearing subject followed by conducting positron emission tomography (PET) scan of the subject to determine an amount of uptake of [$^{18}$F]GE-226 in the subject,
   (b) administering a first amount of a HSP90 inhibitor to the subject and waiting for at least 24 hours before administering [$^{18}$F]GE-226 to the subject followed by conducting a second PET scan of the subject to determine the amount of uptake of [$^{18}$F]GE-226,
   (c) repeat step (b) with at least one additional amount of the HSP90 inhibitor, and
   (d) comparing the PET scan results from (a)-(c) to monitor the dose dependent response of the subject to HSP90 inhibition.

2. The method of claim 1, wherein the subject is a HER2 expressing cancer patient.

3. The method of claim 1, wherein the subject is a HER2 expressing cancer cell line.

4. The method of claim 1, wherein the HSP90 inhibitor is NVP-AUY922.

5. The method of claim 1, wherein the PET scan is conducted within one hour of [$^{18}$F]GE-226 administration to the patient.

* * * * *